(12) United States Patent
Wang et al.

(10) Patent No.: US 10,668,068 B2
(45) Date of Patent: Jun. 2, 2020

(54) TREATING CANCER WITH DRUG COMBINATIONS

(71) Applicant: The Research Foundation for The State University of New York, Albany, NY (US)

(72) Inventors: Xianhui Wang, Albany, NY (US); Douglas S. Conklin, Niskayuna, NY (US)

(73) Assignee: The Research Foundation For The State University Of New York, Albany, NY (US)

( * ) Notice: Subject to any disclaimer, the term of this patent is extended or adjusted under 35 U.S.C. 154(b) by 0 days.

(21) Appl. No.: 14/877,300

(22) Filed: Oct. 7, 2015

(65) Prior Publication Data
US 2017/0100401 A1   Apr. 13, 2017

(51) Int. Cl.
| A61K 31/517 | (2006.01) |
| A61K 31/519 | (2006.01) |
| A61K 31/505 | (2006.01) |
| A61K 45/06 | (2006.01) |
| A61K 31/5377 | (2006.01) |

(52) U.S. Cl.
CPC .......... *A61K 31/517* (2013.01); *A61K 31/505* (2013.01); *A61K 31/519* (2013.01); *A61K 31/5377* (2013.01); *A61K 45/06* (2013.01)

(58) Field of Classification Search
CPC ... A61K 31/517; A61K 31/519; A61K 31/505
USPC ..................................................... 514/262.1
See application file for complete search history.

(56) References Cited

U.S. PATENT DOCUMENTS

| 4,683,195 | A | 7/1987 | Mullis et al. | 435/6.11 |
| 4,683,202 | A | 7/1987 | Mullis | 435/91.2 |
| 4,965,188 | A | 10/1990 | Mullis et al. | 435/6.12 |
| 2012/0165395 | A1* | 6/2012 | Conklin | A61K 31/7088 514/44 A |
| 2014/0057898 | A1* | 2/2014 | Stefanic | A61K 31/404 514/211.15 |
| 2014/0073593 | A1* | 3/2014 | Conklin | A61K 31/519 514/34 |
| 2014/0288098 | A1* | 9/2014 | Conklin | A61K 31/519 514/262.1 |
| 2015/0044217 | A1* | 2/2015 | Chen | A61K 45/06 424/136.1 |

OTHER PUBLICATIONS

Konecny et al. Cancer Research, 2006, 66(3), p. 1630-1639.*
Agrawal et al. Endocrine-Related Cancer (2005), 12, S135-144.*
Grabinski et al., Invest New Drugs, (2014), 32, p. 1096-1104.*
[No Authors Listed] (2000) "Cancer multidrug resistance," *Nature Biotechnology 18*, IT18-IT20.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Aoki, Y. et al. (1994) "Bruton tyrosine kinase is tyrosine phosphorylated and activated in pre-B lymphocytes and receptor-ligated B cells," *Proceedings of the National Academy of Sciences of the United States of America 91*(22), 10606-10609.
Baselga, J. (2006) "Targeting Tyrosine Kinases in Cancer: The Second Wave," *Science 312*(5777), 1175-1178.
Blume-Jensen, P. et al. (2001) "Oncogenic kinase signalling" *Nature 411*(6835), 355-365.
Brown-Glaberman, U. et al. (2014) "HER2-targeted therapy for early-stage breast cancer: a comprehensive review," *Oncology 28*(4), 281-289.
Bruyere, C. et al. (2011) "Temozolomide modifies caveolin-1 expression in experimental malignant gliomas in vitro and in vivo," *Translational Oncology 4*(2), 92-100.
Buggy, J. J. et al. (2012) "Bruton tyrosine kinase (BTK) and its role in B-cell malignancy," *International Reviews of Immunology 31*(2), 119-132.
Burger, J. A. (2014) "Bruton's tyrosine kinase (BTK) inhibitors in clinical trials," *Current Hematologic Malignancy Reports 9*(1), 44-49.
Byrd, J. C. et al. (2013) "Targeting BTK with ibrutinib in relapsed chronic lymphocytic leukemia," *New England Journal of Medicine 369*(1), 32-42.
Call, J. A. et al. (2008) "Targeted manipulation of apoptosis in cancer treatment," *Lancet Oncology 9*(10), 1002-1011.
Carthew, R. W. (2001) "Gene silencing by double-stranded RNA," *Current Opinion in Cell Biology 13*(2), 244-248.
Chu, D. et al. (2008) "Novel therapies in breast cancer: what is new from ASCO 2008," *Journal of Hematology and Oncology 1*(1), 1-13.
De Placido, S. et al. (2015) "Treatment options in HR(+)/HER2(−) advanced breast cancer patients pretreated with nonsteroidal aromatase inhibitors: what does current evidence tell us?," *Future Oncology 11*(6), 1-7.
Di Paolo, J. A. et al. (2011) "Specific Btk inhibition suppresses B cell- and myeloid cell-mediated arthritis," *Nature Chemical Biology 7*(1), 41-50.
Eifert, C. et al. (2013) "A novel isoform of the B cell tyrosine kinase BTK protects breast cancer cells from apoptosis," *Genes, Chromosomes & Cancer 52*(10), 961-975.
Eroglu, Z. et al. (2014) "Human epidermal growth factor receptor family-targeted therapies in the treatment of HER2-overexpressing breast cancer," *Oncologist 19*(2), 135-150.
Farquhar, D. et al. (1991) "Doxorubicin analogs incorporating chemically reactive substituents," *Journal of Medicinal Chemistry 34*(2), 561-564.
Figueroa-Magalhaes, M. C. et al. (2014) "Treatment of HER2-positive breast cancer," *Breast 23*(2), 128-136.

(Continued)

*Primary Examiner* — Yong L Chu
(74) *Attorney, Agent, or Firm* — Medlen & Carroll, LLP

(57) ABSTRACT

Embodiments of the invention find application in the field of cancer therapy. Receptor protein kinases (RPTKs) transmit extracellular signals across the plasma membrane to cytosolic proteins, stimulating formation of complexes that regulate key cellular functions. Over half of the known tyrosine kinases are implicated in human cancers and are therefore highly promising drug targets.

7 Claims, 22 Drawing Sheets

(56) References Cited

OTHER PUBLICATIONS

Giamas, G. et al. (2010) "Kinases as targets in the treatment of solid tumors," *Cellular Signalling* 22(7), 984-1002.
Gillet, J. P. et al. (2010) "Mechanisms of multidrug resistance in cancer," *Methods in Molecular Biology* 596, 47-76.
Grant, S. et al. (2002) "Roles of ERBB family receptor tyrosine kinases, and downstream signaling pathways, in the control of cell growth and survival," *Frontiers in Bioscience* 7, d376-389.
Hendriks, R. W. et al. (2014) "Targeting Bruton's tyrosine kinase in B cell malignancies," *Nature Reviews Cancer* 14(4), 219-232.
Honigberg, L. A. et al. (2010) "The Bruton tyrosine kinase inhibitor PCI-32765 blocks B-cell activation and is efficacious in models of autoimmune disease and B-cell malignancy," *Proc Natl Acad Sci U S A* 107(29), 13075-13080.
Kawakami, Y. et al. (1994) "Tyrosine phosphorylation and activation of Bruton tyrosine kinase upon Fc epsilon RI cross-linking," *Molecular and Cellular Biology* 14(8), 5108-5113.
Khan, W. N. et al. (1995) "Defective B cell development and function in Btk-deficient mice," *Immunity* 3(3), 283-299.
Kim, E. S. et al. (2015) "Ibrutinib: a review of its use in patients with mantle cell lymphoma or chronic lymphocytic leukaemia," *Drugs* 75(7), 769-776.
Konecny, G. E. et al. (2006) "Activity of the dual kinase inhibitor lapatinib (GW572016) against HER-2-overexpressing and trastuzumab-treated breast cancer cells," *Cancer Research* 66(3), 1630-1639.
Krause, D. S. et al. (2005) "Tyrosine Kinases as Targets for Cancer Therapy," *New England Journal of Medicine* 353(2), 172-187.
Kris, M. G. et al. (2003) "Efficacy of gefitinib, an inhibitor of the epidermal growth factor receptor tyrosine kinase, in symptomatic patients with non-small cell lung cancer: A randomized trial," *JAMA: The Journal of the American Medical Association* 290(16), 2149-2158.
Li, Z. et al. (1997) "Phosphatidylinositol 3-kinase-gamma activates Bruton's tyrosine kinase in concert with Src family kinases," *Proceedings of the National Academy of Sciences of the United States of America* 94(25), 13820-13825.
Lovitt, C. J. et al. (2015) "Evaluation of chemotherapeutics in a three-dimensional breast cancer model," *Journal of Cancer Research and Clinical Oncology* 141(5), 951-959.
MacKeigan, J. P. et al. (2005) "Sensitized RNAi screen of human kinases and phosphatases identifies new regulators of apoptosis and chemoresistance," *Nature Cell Biology* 7(6), 591-600.
Mohamed, A. J. et al. (2009) "Bruton's tyrosine kinase (Btk): function, regulation, and transformation with special emphasis on the PH domain," *Immunological Reviews* 228(1), 58-73.
Moritz, A. et al. (2010) "Akt-RSK-S6 kinase signaling networks activated by oncogenic receptor tyrosine kinases," *Science Signaling* 3(136), ra64.
Nahta, R. et al. (2006) "HER2 therapy: Molecular mechanisms of trastuzumab resistance," *Breast Cancer Research* 8(6), 1-8.
Needleman, S. B. et al. (1970) "A general method applicable to the search for similarities in the amino acid sequence of two proteins," *Journal of Molecular Biology* 48(3), 443-453.
O'Brien, S. et al. (2014) "Ibrutinib as initial therapy for elderly patients with chronic lymphocytic leukaemia or small lymphocytic lymphoma: an open-label, multicentre, phase 1b/2 trial," *Lancet Oncology* 15(1), 48-58.
Pan, Z. et al. (2007) "Discovery of selective irreversible inhibitors for Bruton's tyrosine kinase," *ChemMedChem* 2(1), 58-61.

Pearson, W. R. et al. (1988) "Improved tools for biological sequence comparison," *Proceedings of the National Academy of Sciences* 85(8), 2444-2448.
Rabindran, S. K. et al. (2004) "Antitumor activity of HKI-272, an orally active, irreversible inhibitor of the HER-2 tyrosine kinase," *Cancer Research* 64(11), 3958-3965.
Rolli, V. et al. (2002) "Amplification of B cell antigen receptor signaling by a Syk/ITAM positive feedback loop," *Molecular Cell* 10(5), 1057-1069.
Sabbah, M. et al. (2008) "Molecular signature and therapeutic perspective of the epithelial-to-mesenchymal transitions in epithelial cancers," *Drug Resistance Updates* 11(4-5), 123-151.
Sagiv-Barfi, I. et al. (2015) "Therapeutic antitumor immunity by checkpoint blockade is enhanced by ibrutinib, an inhibitor of both BTK and ITK," *Proceedings of the National Academy of Sciences of the United States of America* 112(9), E966-972.
Saito, K. et al. (2001) "Interaction between the Btk PH domain and phosphatidylinositol-3,4,5-trisphosphate directly regulates Btk," *Journal of Biological Chemistry* 276(19), 16201-16206.
Saito, K. et al. (2003) "BTK regulates PtdIns-4,5-P2 synthesis: importance for calcium signaling and PI3K activity," *Immunity* 19(5), 669-678.
Sambrook, J. et al. (1989) "Transfer and Fixation of Denatured RNA to Membranes," in *Molecular Cloning: A Laboratory Manual* (Sambrook, J., et al., Eds.) 2nd ed., pp. 7.39-.52, Cold Spring Harbor Laboratory Press, New York.
Sambrook, J. et al. (1989) "Synthesis of Single-stranded RNA Proves by In Vitro Transcription," in *Molecular Cloning: A Laboratory Manual* (Sambrook, J., et al., Eds.) 2nd ed., pp. 9.31-.58, Cold Spring Harbor Laboratory Press, New York.
Shepard, H. M. et al. (2008) "Signal integration: a framework for understanding the efficacy of therapeutics targeting the human EGFR family," *Journal of Clinical Investigation* 118(11), 3574-3581.
Smith, C. I. et al. (2001) "The Tec family of cytoplasmic tyrosine kinases: mammalian Btk, Bmx, Itk, Tec, Txk and homologs in other species," *BioEssays* 23(5), 436-446.
Smith, L. et al. (2006) "The analysis of doxorubicin resistance in human breast cancer cells using antibody microarrays," *Molecular Cancer Therapeutics* 5(8), 2115-2120.
Smith, T. F. et al. (1981) "Comparison of biosequences," *Advances in Applied Mathematics* 2(4), 482-489.
Tsukada, S. et al. (1993) "Deficient expression of a B cell cytoplasmic tyrosine kinase in human X-linked agammaglobulinemia," *Cell* 72(2), 279-290.
Vassilev, A. O. et al. (2004) "Therapeutic potential of inhibiting Bruton's tyrosine kinase, (BTK)," *Curr Pharm Des* 10(15), 1757-1766.
Wang, X. et al. (2013) "PPARgamma maintains ERBB2-positive breast cancer stem cells," *Oncogene* 32(49), 5512-5521.
Wang, X. et al. (2007) "KLF8 transcription factor participates in oncogenic transformation," *Oncogene* 26(3), 456-461.
Weigelt, B. et al. (2010) "HER2 signaling pathway activation and response of breast cancer cells to HER2-targeting agents is dependent strongly on the 3D microenvironment," *Breast Cancer Research and Treatment* 122(1), 35-43.
Wilson, T. R. et al. (2012) "Widespread potential for growth-factor-driven resistance to anticancer kinase inhibitors," *Nature* 487(7408), 505-509.
Zhang, W. et al. (2011) "Cancer-stromal interactions: role in cell survival, metabolism and drug sensitivity," *Cancer Biology & Therapy* 11(2), 150-156.

* cited by examiner

```
              481
               ↓
BTK    ...MANGCLL...
EGFR   ...MPFGCLL...
Her2   ...MPYGCLL...
ERBB3  ...LPLGSLL...
ERBB4  ...MPHGCLL...
```

|  | | Her2 expression | | | p-v |
|---|---|---|---|---|---|
|  | | Positive | Negative | Total | |
| BTK-C | Positive | 10 | 8 | 18 | |
|  | Negative | 13 | 19 | 32 | |
|  | Total | 23 | 27 | 50 | < 0.01 |

BTK-A & BTK-C kinase domain

TREATING CANCER WITH DRUG COMBINATIONS

STATEMENT OF GOVERNMENTAL SUPPORT

This invention was made with government support under grant no. CA136658 awarded by the National Institutes of Health. The government has certain rights in the invention.

FIELD OF THE INVENTION

Embodiments of the invention find application in the field of cancer therapy. Receptor protein kinases (RPTKs) transmit extracellular signals across the plasma membrane to cytosolic proteins, stimulating formation of complexes that regulate key cellular functions. Over half of the known tyrosine kinases are implicated in human cancers and are therefore highly promising drug targets.

BACKGROUND OF THE INVENTION

Protein tyrosine kinases (PTKs) mediate the reversible process of tyrosine phosphorylation, providing the signals that activate or block signal transduction pathways that govern cell survival decisions and as such are tightly regulated. Genes that regulate extracellular growth, differentiation and developmental signals are commonly mutated in cancers. Perhaps it is not surprising therefore that PTKs comprise the largest group of dominant oncogenes. Thirty of the 58 receptor protein tyrosine kinases (RPTKs) have been implicated in human cancer (Blume-Jensen and Hunter, 2001 [1]). Less than half of the cytoplasmic protein tyrosine kinases have been associated with tumorigenesis, due not to a less critical role in signal transduction regulation, however, but from an experimental bias that has focused on viral counterparts to gain insight into potential transforming mechanisms (Blume-Jensen and Hunter, 2001 [1]).

In recent years there has been a surge in efforts to discover genes critical to cancer signaling pathways that when inhibited would provide specific anti-cancer therapies (Lu and Chu, 2008 [2]) (Sabbah et al., 2008 [3]). Trastuzumab, (Herceptin), a humanized monoclonal antibody that specifically inhibits the HER2/neu/ErbB-2 (hereafter referred to as ErbB-2) receptor tyrosine kinase, which is amplified and/or over-expressed in 25-30% of metastatic breast cancers, was the first targeted therapy to be approved by the FDA. As a single-agent monotherapy, however, the primary response rate to trastuzumab is low, (12% to 34%) and the rate of primary resistance high, between 66% to 88% (Nahta and Esteva, 2006 [4]). Notably, however, the time to disease progression, response rate and overall survival increase when trastuzumab is used in combination with paclitaxel or docetaxel (Nahta and Esteva, 2006 [4]). Indeed, recent successes in targeting molecules integral to survival pathways in combination with traditional chemotherapeutics has led to significant efforts to identify new drug targets that sensitize the breast cancer cell towards cell death (MacKeigan et al., 2005 [5]); (Call et al., 2008 [6]). Such additional drug targets, specific to or over-expressed in breast cancer cells compared to normal tissues, and known to be functionally relevant, are still needed, as are cancer-specific markers for use in detecting or diagnosing cancer.

While a number of inhibitors have been reported, it is not clear whether they possess the appropriate pharmacological properties to be therapeutically useful. Therefore, there is a continued need for small molecule inhibitors to provide effective inhibition. Such compounds would be extremely useful in treating the disease states where inhibition could play a role.

SUMMARY OF THE INVENTION

Embodiments of the invention find application in the field of cancer therapy. Receptor protein kinases (RPTKs) transmit extracellular signals across the plasma membrane to cytosolic proteins, stimulating formation of complexes that regulate key cellular functions. Over half of the known tyrosine kinases are implicated in human cancers and are therefore highly promising drug targets. In one embodiment, the present invention contemplates targeting with drug combinations (given together or sequentially).

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In one embodiment, the invention relates to a method of treating cancer, comprising: a) providing i) a subject with cancer, ii) a inhibitor of a tyrosine kinase, and iii) an EGFR inhibitor, and b) treating said subject with said inhibitors. In one embodiment, said cancer is breast cancer. In one embodiment, said breast cancer is HER2+ breast cancer. In one embodiment, said tyrosine kinase is Bruton's Tyrosine Kinase. In one embodiment, said tyrosine kinase is a variant of Bruton's Tyrosine Kinase comprising an amino-terminal extension. In one embodiment, said EGFR inhibitor is lapatinib. In one embodiment, said EGFR inhibitor is selected from the group consisting of gefitinib, erlotinib, cetuximab, panitumumab, and vandetanib. In one embodiment, said tyrosine kinase inhibitor is selected from the group consisting of ibrutinib (PCI-32765), AVL-292 and CGI-1746. In one embodiment, said treating said subject with said inhibitors is sequential. In one embodiment, said treating said subject with said inhibitors is simultaneous. In one embodiment, treating with said inhibitors results in reduced proliferation of at least some of said cancer cells within said subject.

In one embodiment, the invention relates to a method of treating cancer, comprising: a) providing i) a subject with cancer and ii) AVL-292, iii) lapatinib, and b) treating said subject with said AVL-292 and lapatinib. In one embodiment, said treating said subject with said inhibitors is sequential. In one embodiment, said treating said subject with said inhibitors is simultaneous. In one embodiment, said cancer is breast cancer. In one embodiment, said breast cancer comprises Her-2 positive cells.

In one embodiment, the invention relates to a method of treating cancer, comprising: a) providing i) AVL-292 and ii) a subject with cancer, wherein said subject has been treated with lapatinib, and b) treating said subject with said AVL-292. In one embodiment, said cancer is breast cancer. In one embodiment, said breast cancer comprises Her-2 positive cells.

In one embodiment, the invention relates to a method of treating cancer, comprising: a) providing i) ibrutinib and ii) a subject with cancer, wherein said subject has been treated with lapatinib, and b) treating said subject with said ibrutinib. In one embodiment, said cancer is breast cancer. In one embodiment, said breast cancer comprises Her-2 positive cells.

In one embodiment, the invention relates to a pharmaceutical anticancer composition comprising AVL-292 and lapatinib.

In one embodiment, the invention relates to a pharmaceutical anticancer composition comprising ibrutinib and lapatinib.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The phrase "chosen from A, B, and C" as used herein, means selecting one or more of A, B, C.

As used herein, absent an express indication to the contrary, the term "or" when used in the expression "A or B," where A and B refer to a composition, disease, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (mRNA, etc.) or phenomenon (such as biological activity, biochemical activity, etc.) means that only the particularly named molecule or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first sample relative to a second sample, mean that the quantity of the substance and/or phenomenon in the first sample is higher than in the second sample by any amount that is statistically significant using any art-accepted statistical method of analysis. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than the quantity of the same substance and/or phenomenon in a second sample. In another embodiment, the quantity of the substance and/or phenomenon in the first sample is at least 25% greater than the quantity of the same substance and/or phenomenon in a second sample. In yet another embodiment, the quantity of the substance and/or phenomenon in the first sample is at least 50% greater than the quantity of the same substance and/or phenomenon in a second sample. In a further embodiment, the quantity of the substance and/or phenomenon in the first sample is at least 75% greater than the quantity of the same substance and/or phenomenon in a second sample. In yet another embodiment, the quantity of the substance and/or phenomenon in the first sample is at least 90% greater than the quantity of the same substance and/or phenomenon in a second sample. Alternatively, a difference may be expressed as an "n-fold" difference.

The terms "reduce," "inhibit," "diminish," "suppress," "decrease," and grammatical equivalents when used in reference to the level of a substance and/or phenomenon in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than the quantity of the same substance and/or phenomenon in a second sample. In another embodiment, the quantity of the substance and/or phenomenon in the first sample is at least 25% lower than the quantity of the same substance and/or phenomenon in a second sample. In yet another embodiment, the quantity of the substance and/or phenomenon in the first sample is at least 50% lower than the quantity of the same substance and/or phenomenon in a second sample. In a further embodiment, the quantity of the substance and/or phenomenon in the first sample is at least 75% lower than the quantity of the same substance and/or phenomenon in a second sample. In yet another embodiment, the quantity of the substance and/or phenomenon in the first sample is at least 90% lower than the quantity of the same substance and/or phenomenon in a second sample. Alternatively, a difference may be expressed as an "n-fold" difference.

A number of terms herein relate to cancer. "Cancer" is intended herein to encompass all forms of abnormal or improperly regulated reproduction of cells in a subject. "Subject" and "patient" are used herein interchangeably, and a subject may be any mammal but is preferably a human. A "reference subject" herein refers to an individual who does not have cancer. The "reference subject" thereby provides a basis to which another cell (for example a cancer cell) can be compared.

The growth of cancer cells ("growth" herein referring generally to cell division but also to the growth in size of masses of cells) is characteristically uncontrolled or inadequately controlled, as is the death ("apoptosis") of such cells. Local accumulations of such cells result in a tumor. More broadly, and still denoting "tumors" herein are accumulations ranging from a cluster of lymphocytes at a site of infection to vascularized overgrowths, both benign and malignant. A "malignant" tumor (as opposed to a "benign" tumor) herein comprises cells that tend to migrate to nearby tissues, including cells that may travel through the circulatory system to invade or colonize tissues or organs at considerable remove from their site of origin in the "primary tumor," so-called herein. Metastatic cells are adapted to penetrate blood vessel wells to enter ("intravasate") and exit ("extravasate") blood vessels. Tumors capable of releasing such cells are also referred to herein as "metastatic." The term is used herein also to denote any cell in such a tumor that is capable of such travel, or that is en route, or that has established a foothold in a target tissue. For example, a metastatic breast cancer cell that has taken root in the lung is referred to herein as a "lung metastasis." Metastatic cells may be identified herein by their respective sites of origin and destination, such as "breast-to-bone metastatic." In the target tissue, a colony of metastatic cells can grow into a "secondary tumor," so called herein.

Primary tumors are thought to derive from a benign or normal cell through a process referred to herein as "cancer progression." According to this view, the transformation of a normal cell to a cancer cell requires changes (usually many of them) in the cell's biochemistry. The changes are reflected clinically as the disease progresses through stages. Even if a tumor is "clonogenic" (as used herein, an accumulation of the direct descendants of a parent cell), the biochemistry of the accumulating cells changes in successive generations, both because the expression of the genes (controlled by so-called "epigenetic" systems) of these cells becomes unstable and because the genomes themselves change. In normal somatic cells, the genome (that is, all the genes of an individual) is stored in the chromosomes of each cell (setting aside the mitochondrial genome). The number of copies of any particular gene is largely invariant from cell to cell. By contrast, "genomic instability" is characteristic of cancer progression. A genome in a cancer cell can gain ("genomic gain") or lose ("genomic loss") genes, typically because an extra copy of an entire chromosome appears ("trisomy") or a region of a chromosome replicates itself ("genomic gain" or, in some cases, "genomic amplification") or drops out when the cell divides. Thus, the "copy number" of a gene or a set of genes, largely invariant among normal cells, is likely to change in cancer cells (referred to herein as a "genomic event"), which affects the total expression of the gene or gene set and the biological behavior ("phenotype") of descendent cells. Thus, in cancer cells, "gene activity" herein is determined not only by the multiple "layers" of epigenetic control systems and signals that call forth expression of the gene but by the number of times that gene appears in the genome. The term "epigenetic" herein refers to any process in an individual that, in operation, affects the expression of a gene or a set of genes in that individual, and stands in contrast to the "genetic" processes that govern the inheritance of genes in successive generations of cells or individuals.

Certain regions of chromosomes, depending upon the specific type of cancer, have proven to be hot spots for genomic gain inasmuch as increases in copy number in the genomes of cells from multiple donors tend to occur in one or a few specific regions of a specific chromosome. Such hot spots are referred to herein as sites of "recurrent genomic gain." The term is to be distinguished from "recurrent cancer," which refers to types of cancer that are likely to recur after an initial course of therapy, resulting in a "relapse." A number of terms herein relate to methods that enable the practitioner to examine many distinct genes at once. By these methods, sets of genes ("gene sets") have been identified wherein each set has biologically relevant and distinctive properties as a set. Devices (which may be referred to herein as "platforms") in which each gene in a significant part of an entire genome is isolated and arranged in an array of spots, each spot having its own "address," enable one to detect, quantitatively, many thousands of the genes in a cell. More precisely, these "microarrays" typically detect expressed genes (an "expressed" gene is one that is actively transmitting its unique biochemical signal to the cell in which the gene resides). Microarray data, inasmuch as they display the expression of many genes at once, permit the practitioner to view "gene expression profiles" in a cell and to compare those profiles cell-to-cell to perform so-called "comparative analyses of expression profiles." Such microarray-based "expression data" are capable of identifying genes that are "over-expressed" (or under-expressed) in, for example, a disease condition. An over-expressed gene may be referred to herein as having a high "expression score."

The aforementioned methods for examining gene sets employ a number of well-known methods in molecular biology, to which references are made herein. A gene is a heritable chemical code resident in, for example, a cell, virus, or bacteriophage that an organism reads (decodes, decrypts, transcribes) as a template for ordering the structures of biomolecules that an organism synthesizes to impart regulated function to the organism. Chemically, a gene is a heteropolymer comprised of subunits ("nucleotides") arranged in a specific sequence. In cells, such heteropolymers are deoxynucleic acids ("DNA") or ribonucleic acids ("RNA"). DNA forms long strands. Characteristically, these strands occur in pairs. The first member of a pair is not identical in nucleotide sequence to the second strand, but complementary. The tendency of a first strand to bind in this way to a complementary second strand (the two strands are said to "anneal" or "hybridize"), together with the tendency of individual nucleotides to line up against a single strand in a complementarily ordered manner accounts for the replication of DNA.

Experimentally, nucleotide sequences selected for their complementarity can be made to anneal to a strand of DNA containing one or more genes. A single such sequence can be employed to identify the presence of a particular gene by attaching itself to the gene. This so called "probe" sequence is adapted to carry with it a "marker" that the investigator can readily detect as evidence that the probe struck a target. As used herein, the term "marker" relates to any surrogate the artisan may use to "observe" an event or condition that is difficult or impossible to detect directly. In some contexts herein, the marker is said to "target" the condition or event. In other contexts, the condition or event is referred to as the target for the marker. Sequences used as probes may be quite small (e.g., "oligonucleotides" of <20 nucleotides) or quite large (e.g., a sequence of 100,000 nucleotides in DNA from a "bacterial artificial chromosome" or "BAC").

A BAC is a bacterial chromosome (or a portion thereof) with a "foreign" (typically, human) DNA fragment inserted in it. BACs are employed in a technique referred to herein as "fluorescence in situ hybridization" or "FISH." A BAC or a portion of a BAC is constructed that has (1) a sequence complementary to a region of interest on a chromosome and (2) a marker whose presence is discernible by fluorescence. The chromosomes of a cell or a tissue are isolated (on a glass slide, for example) and treated with the BAC construct. Excess construct is washed away and the chromosomes examined microscopically to find chromosomes or, more particularly, identifiable regions of chromosomes that fluoresce.

Alternatively, such sequences can be delivered in pairs selected to hybridize with two specific sequences that bracket a gene sequence. A complementary strand of DNA then forms between the "primer pair." In one well-known method, the "polymerase chain reaction" or "PCR," the formation of complementary strands can be made to occur repeatedly in an exponential amplification. A specific nucleotide sequence so amplified is referred to herein as the "amplicon" of that sequence. "Quantitative PCR" or "qPCR" herein refers to a version of the method that allows the artisan not only to detect the presence of a specific nucleic acid sequence but also to quantify how many copies of the sequence are present in a sample, at least relative to a control. As used herein, "qRTPCR" may refer to "quantitative real-time PCR," used interchangeably with "qPCR" as a technique for quantifying the amount of a specific DNA sequence in a sample. However, if the context so admits, the same abbreviation may refer to "quantitative reverse transcriptase PCR," a method for determining the amount of messenger RNA present in a sample. Since the presence of a particular messenger RNA in a cell indicates that a specific gene is currently active (being expressed) in the cell, this quantitative technique finds use, for example, in gauging the level of expression of a gene.

Collectively, the genes of an organism constitute its genome. The term "genomic DNA" may refer herein to the entirety of an organism's DNA or to the entirety of the nucleotides comprising a single gene in an organism. A gene typically contains sequences of nucleotides devoted to coding ("exons"), and non-coding sequences that contribute in one way or another to the decoding process ("introns").

The term "gene" refers to a nucleic acid (e.g., DNA) comprising covalently linked nucleotide monomers arranged in a particular sequence that comprises a coding sequence necessary for the production of a polypeptide or precursor or RNA (e.g., tRNA, siRNA, rRNA, etc.). The polypeptide can be encoded by a full-length coding sequence or by any portion of the coding sequence so long as the desired activities or functional properties (e.g., enzymatic activity, ligand binding, signal transduction, etc.) of the full-length or fragment are retained. The term also encompasses the coding region together with the sequences located adjacent to the coding region on both the 5' and 3' ends, such that the gene corresponds to the length of the full-length mRNA (also referred to as "pre-mRNA," "nuclear RNA," or "primary transcript RNA") transcribed from it. The sequences that are located 5' of the coding region and are present on the mRNA are referred to as 5' untranslated sequences. The sequences that are located 3' or downstream of the coding region and that are present on the mRNA are referred to as 3' untranslated sequences. The term "gene" encompasses both cDNA (the coding region(s) only) and genomic forms of a gene. A genomic form or clone of a gene contains the coding region, which may be interrupted with non-coding sequences termed "introns" or "intervening regions" or "intervening sequences." Introns are removed or "spliced out" from the nuclear or primary transcript, and are therefore absent in the messenger RNA (mRNA) transcript. The mRNA functions during translation to specify the sequence or order of amino acids in a nascent polypeptide.

Encoding in DNA (and messenger RNA) is accomplished by 3-membered nucleotide sequences called "codons." Each codon encrypts an amino acid, and the sequence of codons encrypts the sequence of amino acids that identifies a particular protein. The code for a given gene is embedded in a (usually) much longer nucleotide sequence and is distinguishable to the cell's decoding system from the longer sequence by a "start codon" and a "stop" codon. The decoding system reads the sequence framed by these two codons (the so-called "open reading frame"). The readable code is transcribed into messenger RNA which itself comprises sites that ensure coherent translation of the code from nucleic acid to protein. In particular, the open reading frame is delimited by a so-called "translation initiation" codon and "translation termination" codon.

The term "plasmid" as used herein, refers to a small, independently replicating, piece of DNA. Similarly, the term "naked plasmid" refers to plasmid DNA devoid of extraneous material typically used to effect transfection. As used herein, a "naked plasmid" refers to a plasmid substantially free of calcium-phosphate, DEAE-dextran, liposomes, and/or polyamines. As used herein, the term "purified" refers to molecules (polynucleotides or polypeptides) that are removed from their natural environment, isolated or separated. "Purified" molecules are at least 50% free, preferably at least 75% free, and more preferably at least 90% free from other components with which they are naturally associated.

The term "recombinant DNA" refers to a DNA molecule that is comprised of segments of DNA joined together by means of molecular biology techniques. Similarly, the term "recombinant protein" refers to a protein molecule that is expressed from recombinant DNA.

The term "fusion protein" as used herein refers to a protein formed by expression of a hybrid gene made by combining two gene sequences. Typically this is accomplished by cloning a cDNA into an expression vector in frame (i.e., in an arrangement that the cell can transcribe as a single mRNA molecule) with an existing gene. The fusion partner may act as a reporter (e.g., (βgal) or may provide a tool for isolation purposes (e.g., GST).

Where an amino acid sequence is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Rather the terms "amino acid sequence" and "protein" encompass partial sequences, and modified sequences.

The term "wild type" refers to a gene or gene product that has the characteristics of that gene or gene product when isolated from a naturally occurring source. A wild type gene is the variant most frequently observed in a population and is thus arbitrarily designed the "normal" or "wild-type" form of the gene.

In contrast, the terms "modified," "mutant," and "variant" (when the context so admits) refer to a gene or gene product that displays modifications in sequence and or functional properties (i.e., altered characteristics) when compared to the wild-type gene or gene product. In some embodiments, the modification comprises at least one nucleotide insertion, deletion, or substitution.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to reduction in binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target. When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" when used in reference to a first and a second polypeptide means that the first polypeptide with an activity binds to the same substrate as does the second polypeptide with an activity. In one embodiment, the second polypeptide is a variant of the first polypeptide (e.g., encoded by a different allele) or a related (e.g., encoded by a homolog) or dissimilar (e.g., encoded by a second gene having no apparent relationship to the first gene) polypeptide. The efficiency (e.g., kinetics or thermodynamics) of binding by the first polypeptide may be the same as or greater than or less than the efficiency of substrate binding by the second polypeptide. For example, the equilibrium binding constant ($K_D$) for binding to the substrate may be different for the two polypeptides.

As used herein, the term "hybridization" refers to the pairing of complementary nucleic acids. Hybridization and the strength of hybridization (i.e., the strength of the association between the nucleic acids) is impacted by such factors as the degree of complementarity between the nucleic acids, stringency of the conditions involved, the $T_1$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in Nucleic Acid Hybridization [1985] [7]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with 85-100% identity, preferably 70-100% identity). With medium stringency conditions, nucleic acid base pairing will occur between nucleic acids with an intermediate frequency of complementary base sequences (e.g., hybridization under "medium stringency" conditions may occur between homologs with 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 100 to about 1000 nucleotides in length is employed.

"Medium stringency conditions" when used in reference to nucleic acid hybridization comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0× SSPE, 1.0% SDS at 42° C. when a probe of about 100 to about 1000 nucleotides in length is employed.

"Low stringency conditions" comprise conditions equivalent to binding or hybridization at 42° C. in a solution comprising 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a frill-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math., 2: 482, 1981 [8]) by the homology alignment algorithm of Needleman and Wunsch (Needleman and Wunsch, I Mol. Biol. 48:443, 1970 [9]), by the search for similarity method of Pearson and Lipman (Pearson and Lipman, Proc. Natl. Acad. Sci., U.S.A., 85:2444, 1988 [10]), by computerized implementations of these algorithms (GAP, BESTFIT, FASTA, and TFASTA in the Wisconsin Genetics Software Package Release 7.0, Genetics Computer Group, Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic hydroxyl side chains is serine and threonine; a group of amino acids having amide-containing side chains is asparagine and glutamine; a group of amino acids having aromatic side chains is phenylalanine, tyrosine, and tryptophan; a group of amino acids having acidic side chains is glutamic acid and aspartic acid; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Amplification" is used herein in two different ways. A given gene typically appears in a genome once, on one chromosome. Since chromosomes in somatic cells of eukaryotes are in general paired, two copies or alleles of each gene are found. In some conditions, such as cancer, replication of chromosome pairs during cell division is disturbed so that multiple copies of a gene or chromosome accrue over successive generations. The phenomenon is referred to generally (and herein) as "amplification."

In the context of molecular biological experimentation, the term is used differently. Experimentally, "amplification" is used in relation to a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under the conditions in which they are used, will process only specific sequences of nucleic acids in a heterogeneous mixture of nucleic acids. In particular, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of Mullis (U.S. Pat. No. 4,683,195 [11], U.S. Pat. No. 4,683,202 [12], and U.S. Pat. No. 4,965,188 [13], hereby incorporated by reference), that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "restriction endonucleases" and "restriction enzymes" refer to bacterial enzymes, each of which cut double-stranded DNA at or near a specific nucleotide sequence.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding gene includes, by way of example, such nucleic acid in cells ordinarily expressing gene where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The terms "fragment" and "portion" when used in reference to a nucleotide sequence (as in "a portion of a given nucleotide sequence") refers to partial segments of that sequence. The fragments may range in size from four nucleotides to the entire nucleotide sequence minus one nucleotide (10 nucleotides, 20, 30, 40, 50, 100, 200, etc.).

Similarly, the terms "fragment" and "portion" when used in reference to a polypeptide sequence refers to partial segments of that sequence. In some embodiments, the portion has an amino-terminal and/or carboxy-terminal deletion as compared to the native protein, but where the remaining amino acid sequence is identical to the corresponding positions in the amino acid sequence deduced from a full-length cDNA sequence. Fragments are preferably at least 4 amino acids long, more preferably at least 50 amino acids long, and most preferably at least 50 amino acids long or longer (the entire amino acid sequence minus on amino acid). In particularly preferred embodiments, the portion comprises the amino acid residues required for intermolecular binding of the compositions of the present invention with its various ligands and/or substrates.

As used herein the term "portion" when in reference to a protein (as in "a portion of a given protein") refers to fragments of that protein. The fragments may range in size from four consecutive amino acid residues to the entire amino acid sequence minus one amino acid.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

The term "recombinant DNA molecule" as used herein refers to a DNA molecule that is comprised of segments of DNA joined together by means of molecular biological techniques. Similarly, the term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences, that are the native protein contains only those amino acids found in the protein as it occurs in nature. A native protein may be produced by recombinant means or may be isolated from a naturally occurring source.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., Molecular Cloning: A Laboratory Manual, Cold Spring Harbor Press, NY, pp. 9.31-9.58, 1989 [14]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp. 7.39-7.52, 1989 [15]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiola-belled antibodies As used herein, the term "transgenic" refers to a cell or organism whose genome has been heritably altered by genetically engineering into the genome a gene ("transgene") not normally part of it or removing from it a gene ordinarily present (a "knockout" gene). The "transgene" or "foreign gene" may be placed into an organism by introducing it into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term host cell refers to any eukaryotic or prokaryotic cell (e.g. bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell in the sense that the foreign DNA will be passed on to daughter cells. The team encompasses transfections of foreign DNA into the cytoplasm only. In general, however, the foreign DNA reaches the nucleus of the transfected cell and persists there for several days. During this time the foreign DNA is subject to the regulatory controls that govern the expression of endogenous genes in the chromosomes. The term "transient transfectant" refers to cells that have taken up foreign DNA but have failed to integrate this DNA. The term "transient transfection" encompasses transfection of foreign DNA into the cytoplasm only The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of is modified to optimize conditions for particular types of cells. The art is well aware of these numerous modifications.

A "composition comprising a given polynucleotide sequence" as used herein refers broadly to any composition containing the given polynucleotide sequence. Such compositions may be employed as hybridization probes, typically in an aqueous solution containing salts (e.g., NaCl), detergents (e.g., SDS), and other components (e.g., Denhardt's solution, dry milk, salmon sperm DNA, etc.).

The terms "N-terminus" "NH$_2$-terminus" and "amino-terminus" refer to the amino acid residue corresponding to the methionine encoded by the start codon (e.g., position or residue 1). In contrast the terms "C-terminus" "COOH-terminus" and "carboxy terminus" refer to the amino acid residue encoded by the final codon (e.g., last or final residue prior to the stop codon). The term "conservative substitution" as used herein refers to a change that takes place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine). Whether a change in the amino acid sequence of a peptide results in a functional homolog can be readily determined by assessing the ability of the variant peptide to function in a fashion similar to the wild-type protein. Peptides having more than one replacement can readily be tested in the same manner. In contrast, the term "non-conservative substitution" refers to a change in which an amino acid from one family is replaced with an amino acid from another family (e.g., replacement of a glycine with a tryptophan). Guidance in determining which amino acid residues can be substituted, inserted, or deleted without abolishing biological activity can be found using computer programs (e.g., LASERGENE software, DNASTAR Inc., Madison, Wis.

A peptide sequence and nucleotide sequence may be "endogenous" or "heterologous" (i.e., "foreign"). The term "endogenous" refers to a sequence which is naturally found in the cell or virus into which it is introduced so long as it does not contain some modification relative to the naturally-occurring sequence. The term "heterologous" refers to a sequence which is not endogenous to the cell or virus into which it is introduced. For example, heterologous DNA includes a nucleotide sequence which is ligated to, or is manipulated to become ligated to, a nucleic acid sequence to which it is not ligated in nature, or to which it is ligated at a different location in nature. Heterologous DNA also includes a nucleotide sequence which is naturally found in the cell or virus into which it is introduced and which contains some modification relative to the naturally-occurring sequence. Generally, although not necessarily, heterologous DNA encodes heterologous RNA and heterologous proteins that are not normally produced by the cell or virus into which it is introduced. Examples of heterologous DNA include reporter genes, transcriptional and translational regulatory sequences, DNA sequences which encode selectable marker proteins (e.g., proteins which confer drug resistance), etc. In preferred embodiments, the terms "heterologous antigen" and "heterologous sequence" refer to a non-hepadna virus antigen or amino acid sequence including but not limited to microbial antigens, mammalian antigens and allergen antigens.

The terms "peptide," "peptide sequence," "amino acid sequence," "polypeptide," and "polypeptide sequence" are used interchangeably herein to refer to at least two amino acids or amino acid analogs which are covalently linked by a peptide bond or an analog of a peptide bond. The term peptide includes oligomers and polymers of amino acids or amino acid analogs. The term peptide also includes molecules which are commonly referred to as peptides, which generally contain from about two (2) to about twenty (20) amino acids. The term peptide also includes molecules which are commonly referred to as polypeptides, which generally contain from about twenty (20) to about fifty amino acids (50). The term peptide also includes molecules which are commonly referred to as proteins, which generally contain from about fifty (50) to about three thousand (3000) amino acids. The amino acids of the peptide may be L-amino acids or D-amino acids. A peptide, polypeptide or protein may be synthetic, recombinant or naturally occurring. A synthetic peptide is a peptide which is produced by artificial means in vitro.

The terms "oligosaccharide" and "OS" antigen refer to a carbohydrate comprising up to ten component sugars, either 0 or N linked to the next sugar. Likewise, the terms "polysaccharide" and "PS" antigen refer to polymers of more than ten monosaccharide residues linked glycosidically in branched or unbranched chains As used herein, the term "mammalian sequence" refers to synthetic, recombinant or purified sequences (preferably sequence fragments comprising at least one B cell epitope) of a mammal. Exemplary mammalian sequences include cytokine sequence, MHC class I heavy chain sequences, MHC class II alpha and beta chain sequences, and amyloid 13-peptide sequences.

The terms "mammals" and "mammalian" refer animals of the class mammalia which nourish their young by fluid secreted from mammary glands of the mother, including human beings. The class "mammalian" includes placental animals, marsupial animals, and monotrematal animals. An exemplary "mammal" may be a rodent, primate (including simian and human) ovine, bovine, ruminant, lagomorph, porcine, caprine, equine, canine, feline, ave, etc. Preferred non-human animals are selected from the order Rodentia.

Preferred embodiments of the present invention are primarily directed to vertebrate (backbone or notochord) members of the animal kingdom.

The terms "patient" and "subject" refer to a mammal that may be treated using the methods of the present invention.

The term "control" refers to subjects or samples which provide a basis for comparison for experimental subjects or samples. For instance, the use of control subjects or samples permits determinations to be made regarding the efficacy of experimental procedures. In some embodiments, the term "control subject" refers to a subject that which receives a mock treatment (e.g., saline alone).

The terms "diluent" and "diluting agent" as used herein refer to agents used to diminish the strength of an admixture. Exemplary diluents include water, physiological saline solution, human serum albumin, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

The terms "carrier" and "vehicle" as used herein refer to usually inactive accessory substances into which a pharmaceutical substance is suspended. Exemplary carriers include liquid carriers (such as water, saline, culture medium, saline, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins.

The term "derived" when in reference to a peptide derived from a source (such as a microbe, cell, etc.) as used herein is intended to refer to a peptide which has been obtained (e.g., isolated, purified, etc.) from the source. Alternatively, or in addition, the peptide may be genetically engineered and/or chemically synthesized.

The terms "operably linked," "in operable combination" and "in operable order" as used herein refer to the linkage of nucleic acid sequences such that they perform their intended function. For example, operably linking a promoter sequence to a nucleotide sequence of interest refers to linking the promoter sequence and the nucleotide sequence of interest in a manner such that the promoter sequence is capable of directing the transcription of the nucleotide sequence of interest and/or the synthesis of a polypeptide encoded by the nucleotide sequence of interest. Similarly, operably linking a nucleic acid sequence encoding a protein of interest means linking the nucleic acid sequence to regulatory and other sequences in a manner such that the protein of interest is expressed. The term also refers to the linkage of amino acid sequences in such a manner so that a functional protein is produced.

The terms "C-terminal portion," "COOH-terminal portion," "carboxy terminal portion," "C-terminal domain," "COOH-terminal domain," and "carboxy terminal domain," when used in reference to an amino acid sequence of interest refer to the amino acid sequence (and portions thereof that is located from approximately the middle of the amino acid sequence of interest to the C-terminal-most amino acid residue of the sequence of interest. The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule; in other words the second molecule is recognizing and binding to a specific structure on or within the first molecule rather than to nucleic acids or to molecules in general. For example, if a second molecule is specific for structure "A" that is on or within a first molecule, the presence of a third nucleic acid sequence containing structure A will reduce the amount of the second molecule which is bound to the first molecule.

For example, the term "has the biological activity of a specifically named protein" when made in reference to the biological activity of a variant of the specifically named protein refers, for example, to a quantity of binding of an antibody that is specific for the specifically named protein to the variant which is preferably greater than 50% (preferably from 50% to 500%, more preferably from 50% to 200%, most preferably from 50% to 100%), as compared to the quantity of binding of the same antibody to the specifically named protein.

Reference herein to any specifically named nucleotide sequence includes within its scope fragments, homologs, and sequences that hybridize under stringent condition to the specifically named nucleotide sequence. The term "homolog" of a specifically named nucleotide sequence refers to an oligonucleotide sequence which exhibits greater than or equal to 50% identity to the sequence of interest. Alternatively, or in addition, a homolog of any specifically named nucleotide sequence is defined as an oligonucleotide sequence which has at least 95% identity with the sequence of the nucleotide sequence in issue. In another embodiment, the sequence of the homolog has at least 90% identity, and preferably at least 85% identity with the sequence of the nucleotide sequence in issue.

Exons, introns, genes and entire gene-sets are characteristically locatable with respect to one another. That is, they have generally invariant "genomic loci" or "genomic positions." Genes distributed across one or several chromosomes can be mapped to specific locations on specific chromosomes. The field of "cytogenetics" addresses several aspects of gene mapping. First, optical microscopy reveals features of chromosomes that are useful as addresses for genes. In humans, chromosomes are morphologically distinguishable from one another and each (except for the Y-chromosome) has two distinct arms separated by a "centromere." Each arm has distinctive "bands" occupied by specific genes. Disease-related changes in chromosome number and changes in banding form the basis for diagnosing a number of diseases. "Microdissection" of chromosomes and DNA analysis of the microdissected fragments have connected specific DNA sequences to specific locations on chromosomes. In cancer, a region of a chromosome may duplicate or amplify itself or drop out entirely. FISH, mentioned above, and "comparative genomic hybridization" ("CGH") have extended the reach of cytogenetic analysis to the extent of measuring genome alterations within and between individuals. CGH, for example, in which chromosomes from a normal cell are hybridized with a corresponding preparation from a cancer cell provides a means of directly determining cancer-related differences in copy number of chromosomal regions.

"Targeted therapeutics" is used herein to denote any therapeutic modality that affects only or primarily only the cells or tissues selected ("targeted") for treatment. A monoclonal antibody specific for an antigen expressed only by a target (if retained by the target) is highly useful in targeted therapeutics. In the case of unwanted cells such as cancer cells, if the antibody doesn't induce destruction of the target directly, it may do so indirectly by carrying to the target, for example, an agent coupled to the antibody. On the other hand, agents that suppress processes that tend to promote uncontrolled proliferation of cells ("antineoplastic agents") can be delivered to target sites in this manner.

The term "agent" is used herein in its broadest sense to refer to a composition of matter, a process or procedure, a device or apparatus employed to exert a particular effect. By way of non-limiting example, a surgical instrument may be employed by a practitioner as an "excising" agent to remove tissue from a subject; a chemical may be used as a pharmaceutical agent to remove, damage or neutralize the function of a tissue, etc. Such pharmaceutical agents are said to be "anticellular." Cells may be removed by an agent that promotes apoptosis. A variety of toxic agents, including other cells (e.g., cytotoxic T-cell lymphocytes) and their secretions, and a plethora of chemical species, can damage cells.

The term "by-stander", as used herein, refers to a process or event initiated or affected by another, causative event or process.

The term "knockdown", as used herein, refers to a method of selectively preventing the expression of a gene in an individual.

The term "oncogene", as used herein, refers to any gene that regulates a process affecting the suppression of abnormal proliferative events.

The term "single nucleotide polymorphism" or "SNP", as used herein, refers to a DNA sequence variation occurring when a single nucleotide in the genome (or other shared sequence) differs between members of a species or between paired chromosomes in an individual. Single nucleotide polymorphisms may fall within coding sequences of genes, non-coding regions of genes, or in the intergenic regions between genes. Single nucleotide polymorphisms within a coding sequence will not necessarily change the amino acid sequence of the protein that is produced, due to degeneracy of the genetic code. A Single nucleotide polymorphism in which both forms lead to the same polypeptide sequence is termed synonymous (sometimes called a silent mutation)— if a different polypeptide sequence is produced they are non-synonymous. Single nucleotide polymorphisms that are not in protein-coding regions may still have consequences for gene splicing, transcription factor binding, or the sequence of non-coding RNA.

The term "tissue array" or "tissue microarray", as used herein, refers to high throughput platforms for the rapid analysis of protein, RNA, or DNA molecules. These arrays can be used to validate the clinical relevance of potential biological targets in the development of diagnostics, therapeutics and to study new disease markers and genes. Tissue arrays are suitable for genomics-based diagnostic and drug target discovery.

As used herein, the term "shRNA" or "short hairpin RNA" refers to a sequence of ribonucleotides comprising a single-stranded RNA polymer that makes a tight hairpin turn on itself to provide a "double-stranded" or duplexed region. shRNA can be used to silence gene expression via RNA interference. shRNA hairpin is cleaved into short interfering RNAs (siRNA) by the cellular machinery and then bound to the RNA-induced silencing complex (RISC). It is believed that the complex inhibits RNA as a consequence of the complexed siRNA hybridizing to and cleaving RNAs that match the siRNA that is bound thereto.

As used herein, the term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi inhibits the gene by compromising the function of a target RNA, completely or partially. Both plants and animals mediate RNAi by the RNA-induced silencing complex (RISC); a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew has reported (Curr. Opin. Cell Biol. 13(2): 244-248 (2001) [16]) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

As used herein, the term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand"; the strand homologous to the target RNA molecule is the "sense strand", and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "xenograft", as used herein, refers to the transfer or transplant of a cell(s) or tissue from one species to an unlike species (or genus or family).

The term "orthotopic" or "orthotopic xenograft", as used herein, refers to a cell or tissue transplant grafted into its normal place in the body.

The term "fluorescent activated cell sorting" or "FACS", as used herein, refers to a technique for counting, examining, and sorting microscopic particles suspended in a stream of fluid. It allows simultaneous multiparametric analysis of the physical and/or chemical characteristics of single cells flowing through an optical and/or electronic detection apparatus. Generally, a beam of light (usually laser light) of a single wavelength is directed onto a hydro dynamically focused stream of fluid. A number of detectors are aimed at the point where the stream passes through the light beam; one in line with the light beam (Forward Scatter, correlates to cell volume) and several perpendicular to the beam, (Side Scatter, correlates to the inner complexity of the particle and/or surface roughness) and one or more fluorescent detectors. Each suspended particle passing through the beam scatters the light in some way, and fluorescent chemicals found in the particle or attached to the particle may be excited into emitting light at a lower frequency than the light source. By analyzing the combinations of scattered and fluorescent light picked up by the detectors it is then possible to derive information about the physical and chemical structure of each individual particle.

The term "data mining", as used herein, refers to the automated or convenient extraction of patterns representing knowledge implicitly stored or captured in large databases, data warehouses, internet websites, other massive information repositories, or data streams.

The terms "over-express", "over-expressing" and grammatical equivalents, as used herein, refer to the production of a gene product at levels that exceed production in normal or control cells. The term "over-expression" or "highly expressed" may be specifically used in reference to levels of mRNA to indicate a higher level of expression than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed, the amount of 28S rRNA (an abundant RNA transcript present at essentially the same amount in all tissues) present in each sample can be used as a means of normalizing or standardizing the mRNA-specific signal observed on Northern blots. Over-expression may likewise result in elevated levels of proteins encoded by said mRNAs.

The term "heatmap", as used herein, refers to a graphical representation of data where the values obtained from a variable two-dimensional map are represented as colors. As related to the field of molecular biology, heat maps typically represent the level of expression of multiple genes across a number of comparable samples as obtained from a microarray.

The term "phage display", as used herein, refers to the integration/ligation of numerous genetic sequences from a DNA library, consisting of all coding sequences of a cell, tissue or organism library into the genome of a bacteriophage (i.e. phage) for high-throughput screening protein-protein and/or protein-DNA interactions. Using a multiple cloning site, these fragments are inserted in all three possible reading frames to ensure that the cDNA is translated. DNA fragments are then expressed on the surface of the phage particle as part of it coat protein. The phage gene and insert DNA hybrid is then amplified by transforming bacterial cells (such as TG1 *E. coli* cells), to produce progeny phages that display the relevant protein fragment as part of their outer coat. By immobilizing relevant DNA or protein target(s) to the surface of a well, a phage that displays a protein that binds to one of those targets on its surface will remain while others are removed by washing. Those that remain can be eluted, used to produce more phage (by bacterial infection with helper phage) and so produce an enriched phage mixture. Phage eluted in the final step can be used to infect a suitable bacterial host, from which the phagemids can be collected and the relevant DNA sequence excised and sequenced to identify the relevant, interacting proteins or protein fragments.

The term "apoptosis", as used herein, refers to a form of programmed cell death in multicellular organisms that involves a series of biochemical events that lead to a variety of morphological changes, including blebbing, changes to the cell membrane such as loss of membrane asymmetry and attachment, cell shrinkage, nuclear fragmentation, chromatin condensation, and chromosomal DNA fragmentation. Defective apoptotic processes have been implicated in an extensive variety of diseases; for example, defects in the apoptotic pathway have been implicated in diseases associated with uncontrolled cell proliferations, such as cancer. The term "bioluminescence imaging" or "BLI", as used herein, refers to the noninvasive study of ongoing biological processes in living organisms (for example laboratory animals) using bioluminescence, the process of light emission in living organisms. Bioluminescence imaging utilizes native light emission from one of several organisms which bioluminescence. The three main sources are the North American firefly, the sea pansy (and related marine organisms), and bacteria like *Photorhabdus luminescens* and *Vibrio fischeri*. The DNA encoding the luminescent protein is incorporated into the laboratory animal either via a virus or by creating a transgenic animal. While the total amount of light emitted via bioluminescence is typically small and not detected by the human eye, an ultra-sensitive CCD camera can image bioluminescence from an external vantage point. Common applications of BLI include in vivo studies of infection (with bioluminescent pathogens), cancer progression (using a bioluminescent cancer cell line), and reconstitution kinetics (using bioluminescent stein cells).

The term "consensus region" or "consensus sequence", as used herein, refers to the conserved sequence motifs that show which nucleotide residues are conserved and which nucleotide residues are variable when comparing multiple DNA, RNA, or amino acid sequence alignments. When comparing the results of a multiple sequence alignment, where related sequences are compared to each other, and similar functional sequence motifs are found. The consensus sequence shows which residues are conserved (are always the same), and which residues are variable. A consensus sequence may be a short sequence of nucleotides, which is found several times in the genome and is thought to play the same role in its different locations.

For example, many transcription factors recognize particular consensus sequences in the promoters of the genes they regulate. In the same way restriction enzymes usually have palindromic consensus sequences, usually corresponding to the site where they cut the DNA. Splice sites (sequences immediately surrounding the exon-intron boundaries) can also be considered as consensus sequences. In one aspect, a consensus sequence defines a putative DNA recognition site, obtained for example, by aligning all known examples of a certain recognition site and defined as the idealized sequence that represents the predominant base at each position. Related sites should not differ from the consensus sequence by more than a few substitutions.

The term "linkage", or "genetic linkage," as used herein, refers to the phenomenon that particular genetic loci of genes are inherited jointly. The "linkage strength" refers to the probability of two genetic loci being inherited jointly. As the distance between genetic loci increases, the loci are more likely to be separated during inheritance, and thus linkage strength is weaker.

The term "neighborhood score", as used herein, refers to the relative value assigned to a genomic locus based on a geometry-weighted sum of expression scores of all the genes on a given chromosome, as a measurement of the copy number status of the locus. A positive neighborhood score is indicative of an increase in copy number, whereas a negative neighborhood score is indicative of a decrease in copy number.

The term "expression score", as used herein, refers to the expression differences (i.e., the level of transcription (RNA) or translation (protein)) between comparison groups on a given chromosome. The expression score for a given gene is calculated by correlating the level of expression of said gene with a phenotype in comparison. For example, an expression score may represent a comparison of the expression differences of a given gene in normal vs. abnormal conditions, such as parental vs. drug-resistant cell lines. As used herein, the term "regional expression score" refers to the expression score of gene(s) in proximity to the locus in consideration. Since linkage strength between genetic loci decreases (i.e. decays) as the distance between them increases, the "regional expression score" more accurately reflects the expression differences between comparison groups by assigning greater weight to the expression scores of genes in proximity to the locus in consideration.

The terms "geometry-weighted" or "geometry-weighted sum", as used herein, refers to the significance attached to a given value, for example an "expression score", based on physical position, including but not limited to genomic position. Since linkage strength between genetic loci decreases (i.e. decays) as the distance between them increases, the "weight" assigned to a given value is adjusted accordingly.

The term "copy number alteration" or "CNA", as used herein, refers to the increase (i.e. genomic gain) or decrease (i.e. genomic loss) in the number of copies of a gene at a specific locus of a chromosome as compared to the "normal" or "standard" number of copies of said gene that locus. As used herein, an increase in the number of copies of a given gene at a specific locus may also be referred to as an "amplification" or "genomic amplification" and should not be confused with the use of the term "amplification" as it relates, for example, to amplification of DNA or RNA in PCR and other experimental techniques.

The term "clonogenic assay", as used herein, refers to a technique for studying whether a given cancer therapy (for example drugs or radiation) can reduce the clonogenic survival and proliferation of tumor cells. While any type of cell may be used, human tumor cells are commonly used for ontological research. The term "clonogenic" refers to the fact that these cells are clones of one another.

The term "adjuvant therapy", as used herein, refers to additional treatment given after the primary treatment to increase the chances of a cure. In some instances, adjuvant therapy is administered after surgery where all detectable disease has been removed, but where there remains a statistical risk of relapse due to occult disease. If known disease is left behind following surgery, then further treatment is not technically "adjuvant". Adjuvant therapy may include chemotherapy, radiation therapy, hormone therapy, or biological therapy. For example, radiotherapy or chemotherapy is commonly given as adjuvant treatment after surgery for a breast cancer. Oncologists use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been cured by their primary surgery. Adjuvant chemotherapy and radiotherapy are often given following surgery for many types of cancer, including colon cancer, lung cancer, pancreatic cancer, breast cancer, prostate cancer, and some gynecological cancers.

The term "matched samples", as used herein, as for example "matched cancer samples" refers to a sample in which individual members of the sample are matched with every other sample by reference to a particular variable or quality other than the variable or quality immediately under investigation. Comparison of dissimilar groups based on specified characteristics is intended to reduce bias and the possible effects of other variables. Matching may be on an individual (matched pairs) or a group-wide basis.

The term "genomic segments", as used herein, refers to any defined part or region of a chromosome, and may contain zero, one or more genes.

The term "co-administer", as used herein, refers to the administration of two or more agents, drugs, and/or compounds together (i.e. at the same time).

The term "diagnose" or "diagnosis", as used herein, refers to the determination, recognition, or identification of the nature, cause, or manifestation of a condition based on signs, symptoms, and/or laboratory findings.

The term "resistance", as used herein, refers to cancer cells that do not respond to chemotherapy drugs (i.e. chemotherapeutic agents). Typically, a first course of chemotherapy may prove highly beneficial, nearly annihilating a tumor, but a few resistant cancer cells often survive and proliferate. Too often, despite more aggressive second and third courses of chemotherapy, the remaining drug-defiant cells thrive, displaying increasing resistance to drug therapy and eventually displaying virtual invulnerability to chemotherapy. After the drug's effectiveness fades, the patient relapses. This occurs in patients with a variety of blood cancers and solid tumors, including breast, ovarian, lung, and lower gastrointestinal tract cancers. Nature Biotechnology 18:IT18-IT20 (2000) [17]. Resistance to treatment with anticancer drugs results from a variety of factors including individual variations in patients and somatic cell genetic differences in tumors, even those from the same tissue of origin. Frequently resistance is intrinsic to the cancer, but as therapy becomes more and more effective, acquired resistance has also become common. The development of multidrug resistance (MDR) to chemotherapy remains a major challenge in the treatment of cancer. Resistance exists against every effective anticancer drug and can develop by numerous mechanisms including decreased drug uptake, increased drug efflux, activation of detoxifying systems, activation of DNA repair mechanisms, and insensitivity to drug-induced apoptosis. Methods Mol. Biol. 596:47-76 (2010) [18].

In some embodiments, the present invention contemplates treating drug resistant cancer cells. It is not intended that the present invention be limited to the degree of resistance, i.e. resistance can be shown simply by the fact that it takes higher doses of drug to kill these cells. The cells need not be resistant at every dose. The cells may be resistant such that higher doses needed to kill the cells will not be well tolerated by the patient.

As used herein, "Doxorubicin" (trade name Doxil) also known as "hydroxydaunorubicin" or "Adriamycin" refers to a drug used in cancer chemotherapy, that is considered to be the most effective agent in the treatment of breast cancer patients. Doxorubicin is an anthracycline antibiotic, closely related to the natural product daunomycin, and like all anthracyclines, works by intercalating DNA, with the most serious adverse effect being life-threatening heart damage. Doxorubicin is commonly used in the treatment of a wide range of cancers, including some leukemia's and Hodgkin's lymphoma, as well as cancers of the bladder, breast, stomach, lung, ovaries, thyroid, soft tissue sarcoma, multiple myeloma. It is frequently used in breast cancer therapy either as single-agent or in combination with other drugs like docetaxel and cyclophosphamide. Unfortunately, resistance to this agent is common, representing a major obstacle to successful treatment. Mol. Cancer Ther. 5(8):2115-20 (2006) [19]. Doxorubicin is administered intravenously, as the hydrochloride salt. It may be sold under the brand names Adriamycin PFS, Adriamycin RDF, or Rubex. Commonly used doxonibicin-containing regimens include, but are not necessarily limited to, AC (Adriamycin, cyclophosphamide), TAC (taxotere, AC), ABVD (Adriamycin, bleomycin, vinblastine, dacarbazine), BEACOPP (bleomycin, etoposide, Adriamycin, cyclophosphamide, vincristine, procarbazine, prednisone), BEP (bleomycin, etoposide, platinum agent (cisplatin (Platinol)), CAF (cyclophosphamide, Adriamycin, fluorouracil (5-FU)), CAV (cyclophosphamide, Adriamycin, vincristine), CHOP (cyclophosphamide, Adriamycin, vincristine, prednisone), ChlVPP/EVA (chlorambucil, vincristine, procarbazine, prednisone, etoposide, vinblastine, Adriamycin), CVAD/HyperCVAD (cyclophosphamide, vincristine, Adriamycin, dexamethasone), DT-PACE (dexamethasone, thalidomide, cisplatin or platinol, Adriamycin, cyclophosphamide, etoposide), FAC (5-fluorouracil, Adriamycin, cyclophosphamide), m-BACOD (methotrexate, bleomycin, adriamycin, cyclophosphamide, Oncovin (vincristine), dexamethasone), MACOP-B (methotrexate, leucovorin (folinic acid), adriamycin, cyclophosphamide, Oncovin (vincristine), prednisone, bleomycin), ProMACE-MOPP (methotrexate, Adriamycin, cyclophosphamide, etoposide+MOPP), ProMACE-CytaBOM (prednisone, Adriamycin, cyclophosphamide, etoposide, cytarabine, bleomycin, vincristine, methotrexate, leucovorin), VAD (vincristine, Adriamycin, dexamethasone), Regimen I (vincristine, Adriamycin, etoposide, cyclophosphamide) and VAPEC-B (vincristine, Adriamycin, prednisone, etoposide, cyclophosphamide, bleomycin).

Analogues of Doxorubicin for cancer chemotherapy include, but are not limited to, daunorubicin, 4-demethoxydaunorubicin (idarubicin), pirarubicin (DaunoXome), epirubicin, pegylated liposomal doxorubicin (Lipo-Dox®), antibody-conjugated liposomal doxorubicin (e.g. S5A8-Lipo-Dox), 4'-epidoxorubicin, AD198, N-(5,5-Diacetoxypent-1-yl)doxorubicin, and Doxorubicin analogues 2-5, incorporating the following alkylating or latent alkylating substituents, R, on the 3'-position of the daunosamine sugar. 2, R=NHCOC$_6$H$_4$(p)SO$_2$F; 3, R=NHCOCH$_2$Br; 4, R=NHCOCH$_2$Cl; 5, R=NHCON(NO)CH$_2$CH$_2$Cl. *J Med Chem.* 1991 February; 34(2):561-4 [20].

As used herein, "Ibrutinib", also known as PCI-32765, refers to a drug for the treatment of various types of hematopoietic related cancer, and is shown in FIG. 8B. However, in one embodiment, the present invention contemplates the use of ibrutinib for non-hematopoietic related cancers, and in particular for breast cancer.

As used herein, "AVL-292" also known as "Spebrutinib;" "CC-292;" "CC292;" "CC 292;" "AVL292;" "AVL-292;" and "AVL 292" is N-(3-((5-fluoro-2((4-(2-methoxyethoxy)phenyl)amino)pyrimidin-4-yl)amino)phenyl)acrylamide, has CAS#: 1202757-89-8, and is shown in FIG. 8B.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1A shows cell counts of MCF-10A, MCF7, SKBR3 and MDA-MB-231 cells treated with vehicle, 1 μM and 10 μM of ibrutinib (Ibr) for 3 days.

FIG. 1B shows cell counts of SKBR3 and BT474 cells treated with vehicle and different concentration of ibrutinib, as indicated for 3 days.

FIG. 1C shows cell counts of BT474 cells treated with vehicle and ibrutinb, AVL-292 and CGI-1746, as indicated concentration, for 3 days. Results are presented as percentage of control (vehicle). Error bars indicate the s.d. from three individual experiments, *p<0.05, **p<0.01 compare with control.

FIG. 2A shows cell counts of BT474 cells treated with vehicle, lapatinib(Lap) and ibrutinib(Ibr) for 3 days. Results are presented as percentage of control (vehicle). Error bars indicate the s.d. from three individual experiments, *p<0.05, **p<0.01 compare with control.

FIG. 2B shows BT474 cells were treated with laptanib and ibrutinib, as indicated, for 9 days on Matrigel culture condition.

FIG. 2C shows the alignment of EGFR family members with BTK.

FIG. 2D shows the effects of BTK inhibitors on EGFR family activation. BT474 cells were treated with different concentration of BTK inhibitors ibrutinib and AVL-292 or laptinib for 2 h. Whole cell lysates were prepared for Western blotting using antibody against p-EGFR, p-Her2, p-ERBB3, p-ERBB4, p-Akt, p-ERK protein. Anti-AKT and anti-ERK blotting were done as loading controls.

FIG. 3A shows the effect of ibrutinib and lapatinib on cell cycle progression. BT474 cells were treated with the indicated concentration of ibrutinib and lapatinib for 16 h. Cells were stained with propidium iodide and analyzed by flow cytometry.

FIG. 3B show BT474 cells were treated with ibrutinib or lapatinib for 16 h. Cell lysates were analyzed by western blotting using anti-cyclin D1, anti-p27 antibodies, anti-ERK as loading control.

FIG. 3C shows Bt474 cells were treated with ibrutinib or lapatinib for 16 h. Apoptotic cells were identified by Alexa Fluor 488 Annexin V kit. *p<0.05, **p<0.01 compare with control.

FIG. 3D shows immunoblots showing apoptosis in BT474 cells after indicated concentration of ibrutinib treatment for 16 h.

FIG. 4A shows live cell count assay showing the NRG effects on drug-treated BT474 cells (72 h), complete rescue, lapatinib (Lap) with NRG treatment; no rescue lapatinib, ibrutinib(Ibr) and ibrutinib with NRG treatment.

FIG. 4B shows crystal violet cell staining of BT474 or SKBR3 cells treated with lapatinib (1 uM) with or without NRG1 (50 ng/ml), ibrutinib (1 uM) with or without NRG (50 ng/ml).

FIG. 4C shows immunoblots showing effects of NRG (50 ng/ml) on p-AKT and a-ERK after cells treated with lapatinib or ibrutinib (2 h) in BT474 and SkBR3 cells.

FIG. 4D shows a live cell count assay showing the NRG effects on drug-treated BT474 cells (72 h), complete rescue, Lapatinib with NRG1 treatment; no rescue, lapatinib alone or lapatinib and AVL with NRG1 treatment.

FIG. 5A shows SKBR3-BTKC cells were treated with ibrutinib, LY294002 and Saracatinib as indicated concentration for 24 h. Cell lysates were tested for p-BTK, p-AKT and p-ERK. Anti-flag as loading control.

FIG. 6A shows images of tumors formed in animals after mammary fat pad injection of SKBR3 cancer cells. Animals were treated with vehicle, lapatinib (37.5 mg/kg or 75 mg/kg) or ibrutinib (6 mg/kg or 12 mg/kg) for 4 weeks.

FIG. 6B shows tumor growth curves obtained following fat pad injection of SKBR3 cells. The data represent the mean±s.e. (n=5, *P<0.01).

FIG. 6C shows histological analysis of tumors from SKBR3 cells treated with ibrutinib (12 mg/kg) or vehicle. Shown are pHH3, caspase 3, pHer2, pBTK, pAkt and pErk staining.

FIG. 7A shows Her2 positive and negative surgical specimens of human breast tumors (BR10010b) were subject to stain BTK and Her2. The data represent 50 of breast tumor specimens. Case 1 and case 2 represent positive staining BTK-C, case 1 and case 3 represent positive staining Her2.

DETAILED DESCRIPTION OF THE INVENTION

Figure 1A:
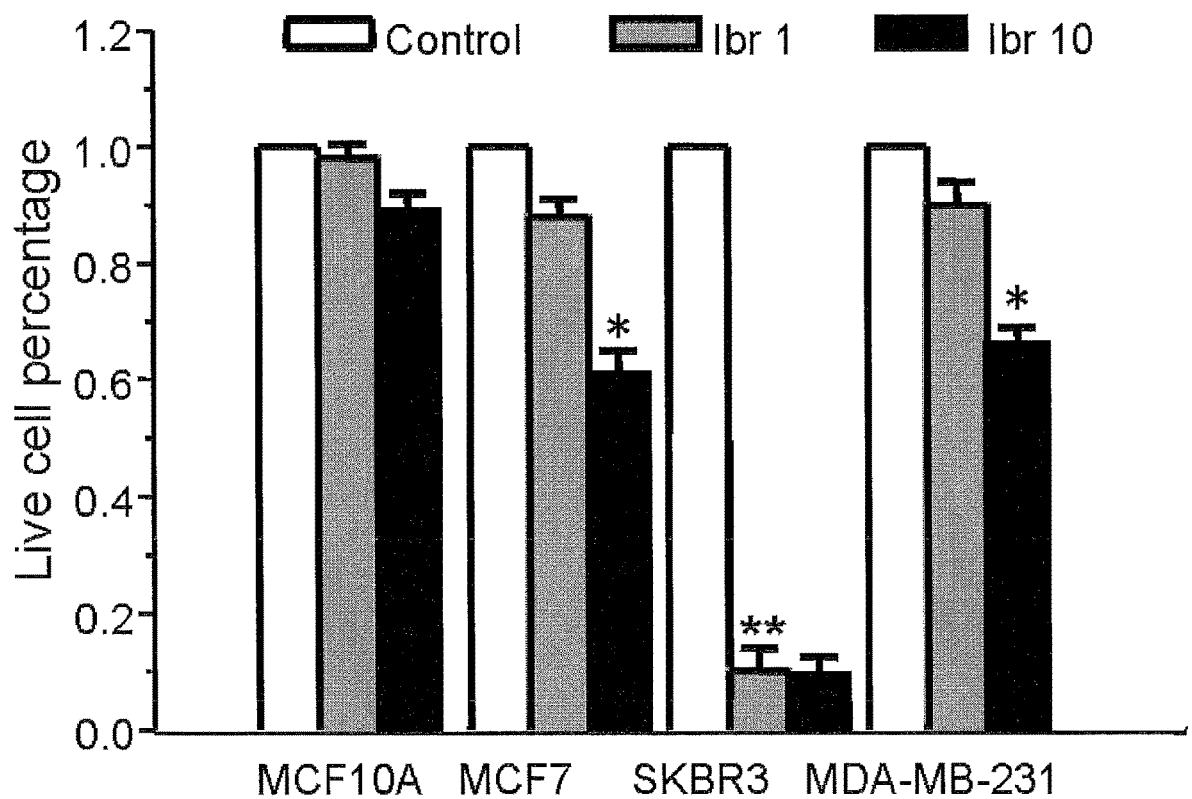
FIG. 1A-C show growth inhibitory effects of BTK inhibitors on breast cancer cell lines.

Tyrosine kinases (TKs) catalyze the reversible process of tyrosine phosphorylation, a key step in most signal transduction pathways that govern cellular proliferation, survival, differentiation, and motility. Dysregulation of TKs, as occurs through inappropriate expression, activation, or both, is commonly associated with human cancers (Blume-Jensen and Hunter 2001 [1]; Giamas, et al. 2010 [21]). As a result, TKs, as a class, are the most commonly found dominant oncogenes (Baselga 2006 [22]; Blume-Jensen and Hunter 2001 [1]; Krause and Van Etten 2005 [23]; Vassilev and Uckun 2004 [24]). Receptor protein tyrosine kinases (RPTKs) transmit extracellular signals across the plasma membrane to cytosolic proteins, stimulating the formation of complexes that regulate key cellular functions. Over half of the 90 tyrosine kinases have been implicated in human cancers and are for this reason considered highly promising drug targets. To gain insight into the tyrosine kinases that contribute to breast cancer related cellular mechanisms, we carried out a large-scale loss-of-function analysis of the tyrosine kinases, using RNA interference, in the clinically relevant Erb-B2 positive, BT474 breast cancer cell line. The cytosolic, non-receptor tyrosine kinase Bruton's tyrosine kinase (BTK), which has been extensively studied for its role in B cell development, was among those tyrosine kinase genes required for BT474 breast cancer cell survival. The BTK protein identified was an alternative form containing an amino-terminal extension. This alternative form of the Btk message is also present in tumorigenic breast cells at significantly higher levels than in normal breast cells.

Small molecules that directly inhibit the catalytic activity of tyrosine kinases have been sought as potential cancer chemotherapeutics. Recent successes with a few well-studied tyrosine kinases have proven the value of these proteins as drug targets. Imatinib mesylate (Gleevec) has proven hugely successful in treating CML. The EGFR inhibitors, Gefitinib (Iressa) and erlotinib (Tarceva), are currently used on a variety of solid tumors (Krause and Van Etten 2005 [23]; Kris, et al. 2003 [25]; Shepard, et al. 2008 [26]). Trastuzumab (Herceptin), a humanized monoclonal antibody that specifically inhibits Erb-B2, is widely used in the treatment of breast cancers. Each of these treatments, however, has significant limitations related to tissue spectrum, acquired resistance, and efficacy in advanced disease (Nahta and Esteva 2006 [4]). The identification of additional TK genes and pathways that contribute to the survival of distinct cancer cell types, so that they can be effectively targeted, would be of great value.

Bruton's tyrosine kinase (BTK) is a key player in B cell development as well as an important regulator of cell proliferation and cell survival in various B cell malignancies. It has been reported that an isoform of BTK (BTK-C) expressed in breast cancer protects these cells from apoptosis. Herein, the effect of recently developed inhibitors of BTK on breast cancer cells are tested. Inhibitors of BTK such as ibrutinib (PCI-32765), AVL-292 and CGI-1746 show reduction of the survival of breast cancer cell lines in vitro. It was found that ibrutinib treatment significantly decreases the viability of HER2+ breast cancer cell lines in vitro at lower concentrations than the established breast cancer therapeutic lapatinib. It is thought that this may be due in part to the inhibition of EGFR family activation in addition to its effect on BTK-C. Herein it is demonstrated that ibrutinib, but not AVL-292 and CGI-1746, efficiently blocks activation of EGFR, HER2, ErbB3, and ErbB4. Consequently, the activation of AKT and ERK signaling pathways are also blocked leading to an appreciable G1/S cell cycle delay, decreased cell proliferation and increased levels of apoptosis. NRG and EGF have been shown to reactivate the AKT signaling pathway and promote the growth factor-driven resistance that rescues HER2+ breast cancer cells from the antiproliferative effects of lapatinib. Ibrutinib, however, inhibits AKT re-activation by NRG or EGF. Consequently, HER2+ breast cancer cell proliferation remains blocked by ibrutinib even in the presence of these factors Importantly, although AVL-292 has no effect on EGFR family activation, it prevents NRG- and EGF-dependent growth factor driven resistance to lapatinib in HER2+ breast cancer cells suggesting that BTK activity is important in this process. In vivo, ibrutinib inhibits SKBR3 xenograft tumor growth. Immunofluorescence staining of tumor tissues shows that ibrutinib blocks the phosphorylation of Her2, BTK, Akt and Erk which result in decreased histone 3 phosphorylation and increased caspase-3 signals Since it is also shown that BTK-C and HER2 are often co-expressed in human breast cancer, these observations indicate that BTK-C is a potential therapeutic target and that ibrutinib could be an effective drug, especially for HER2+ breast cancer.

Introduction

Bruton's tyrosine kinase (BTK) belongs to the TEC family, of cytoplasmic tyrosine kinases [27]. It was identified in 1993 as a novel non-receptor protein tyrosine kinase that is mutated in X-linked agammaglobulinaemia (XLA) [28, 29]. BTK is predominantly expressed in hematopoietic cells including erythroid progenitors and myeloid cells[30]. BTK is a critical regulator of B cell receptor signaling. Studies have established that BTK has a crucial role for B-cell development, differentiation, survival and signal transduction [31-33]. Due to its role in BCR signaling induced proliferation, BTK has emerged as a novel target for the treatment of rheumatoid arthritis and other immune diseases. Recent studies have focused on the essential role of BTK in many B cell leukaemias and lymphomas [34, 35] which provides a rationale for targeting the kinase in these malignancies. Second generation BTK inhibitors including ibrutinib, AVL-292 and CGI-1746 were developed as immunosuppressants and have been used in clinical trials for blood malignancies[36]. Recently, ibrutinib (Imbruvica) gained FDA approval for the treatment of mantle cell lymphoma, chronic lymphocytic leukemia, and Waldenström's macroglobulinemia [37]. An alternate isoform of BTK, BTK-C, was identified as a novel survival factor for breast cancer cells in a large-scale loss-of-function analysis of human tyrosine kinases using an RNA interference library [38]. This study showed that although BTK is expressed at relatively low levels in several human breast cancer cell lines and tumor tissues, it provides an essential function protecting breast cancer cells from apoptosis.

It has long been appreciated that HER2 is overexpressed or amplified in tumors of about 20% of patients with early stage breast cancer and confers an increased disease recurrence and a worse prognosis [39]. HER2-directed therapies including trastuzumab, pertuzumab, ado-trastuzumab and lapatinib have been used in clinic and has significantly improved the outlook for patients with HER2-positive breast cancer [40]. However, a significant proportion of these patients still relapses and succumbs to their disease [41]. Therefore, new classes of drugs are needed, especially for HER2-positive advanced-stage breast cancer and those that have developed resistance to current therapies.

Herein the effects of treating HER2-positive breast cancer cells with a potent, irreversibly-acting small molecule inhibitor of BTK, ibrutinib is described. It is shown that ibrutinib induces G1-S arrest and apoptosis in breast cancer cells. The effects of ibrutinib on HER2-positive breast cancer cells are shown to be not sensitive to stimulation with NRG1 or EGF as occurs with lapatinib. As the expression of BTK-C and HER2 are positively correlated in surgical specimens of human breast cancer tissues, these results indicate that ibrutinib is a potential therapy for this solid tumor type.

Results

Activity of STK Inhibitors in Human Breast Cancer Cells

Figure 1B:
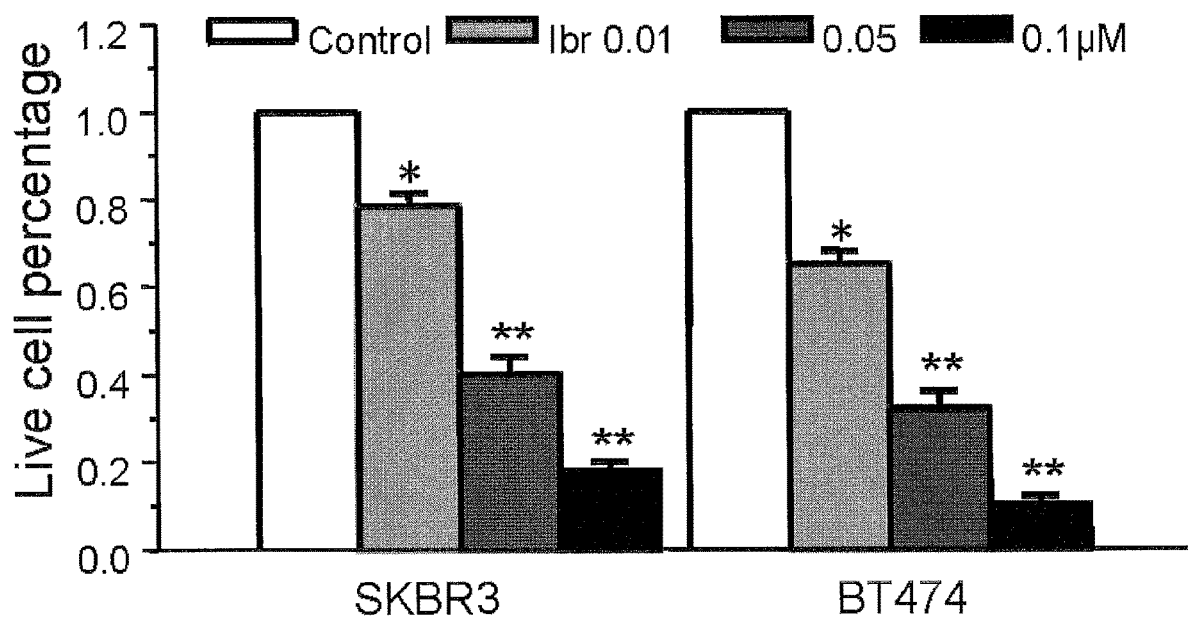
Figure 1C:
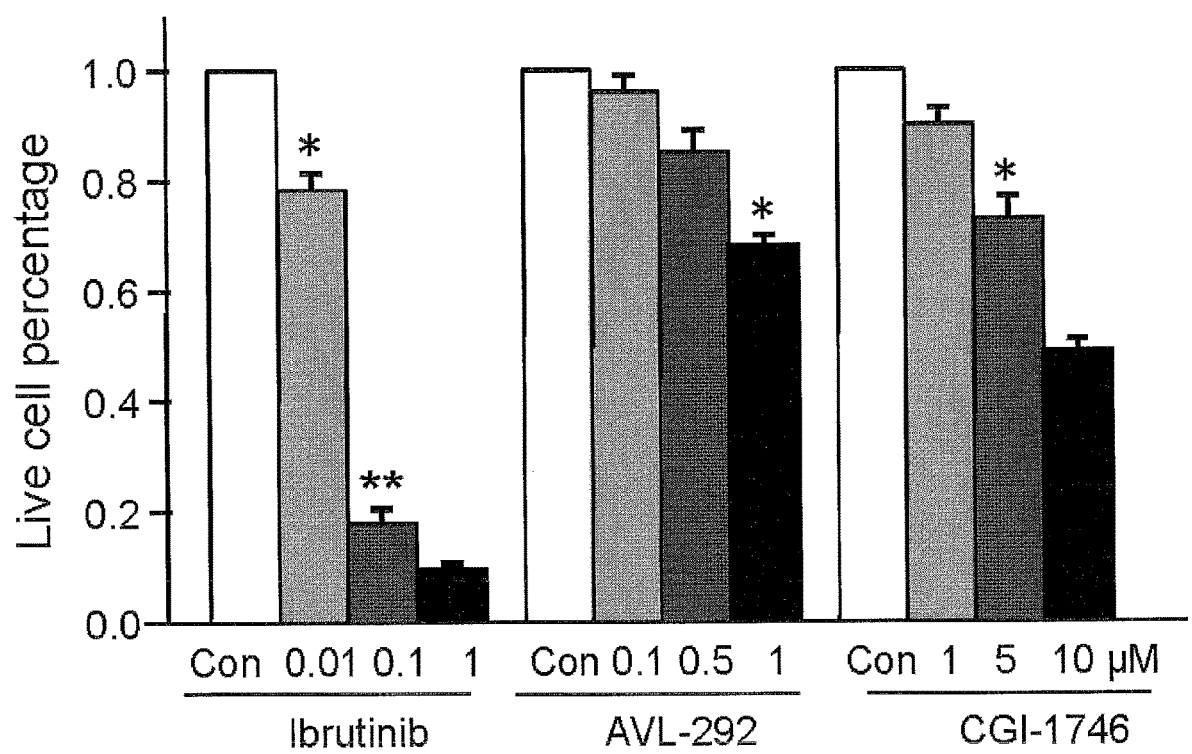
Figure 8A:
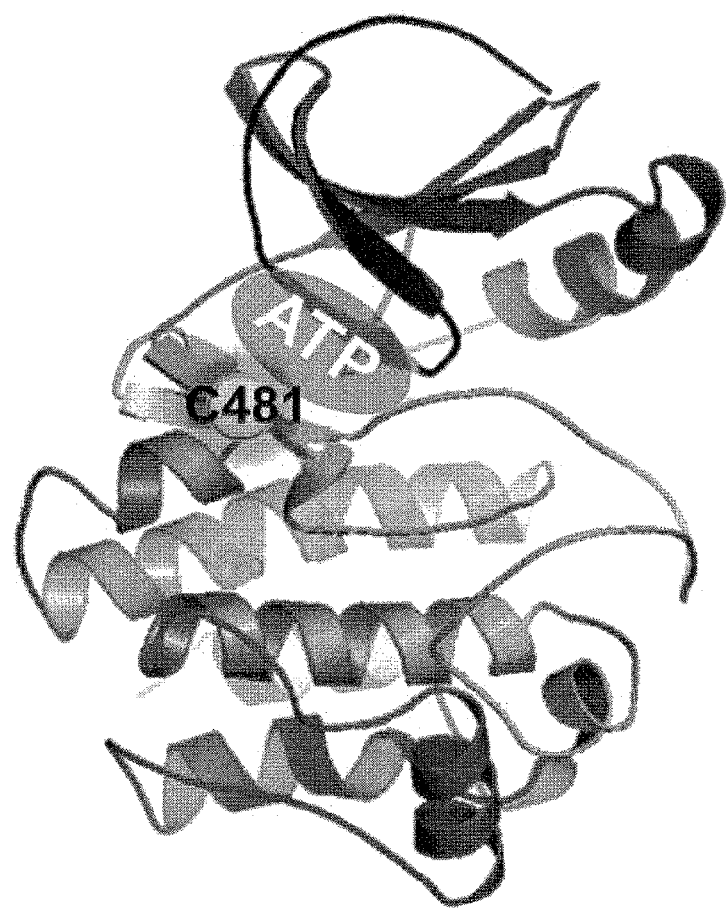
FIG. 8A shows the BTK-A & BTK-C kinase domain.
Figure 8B:
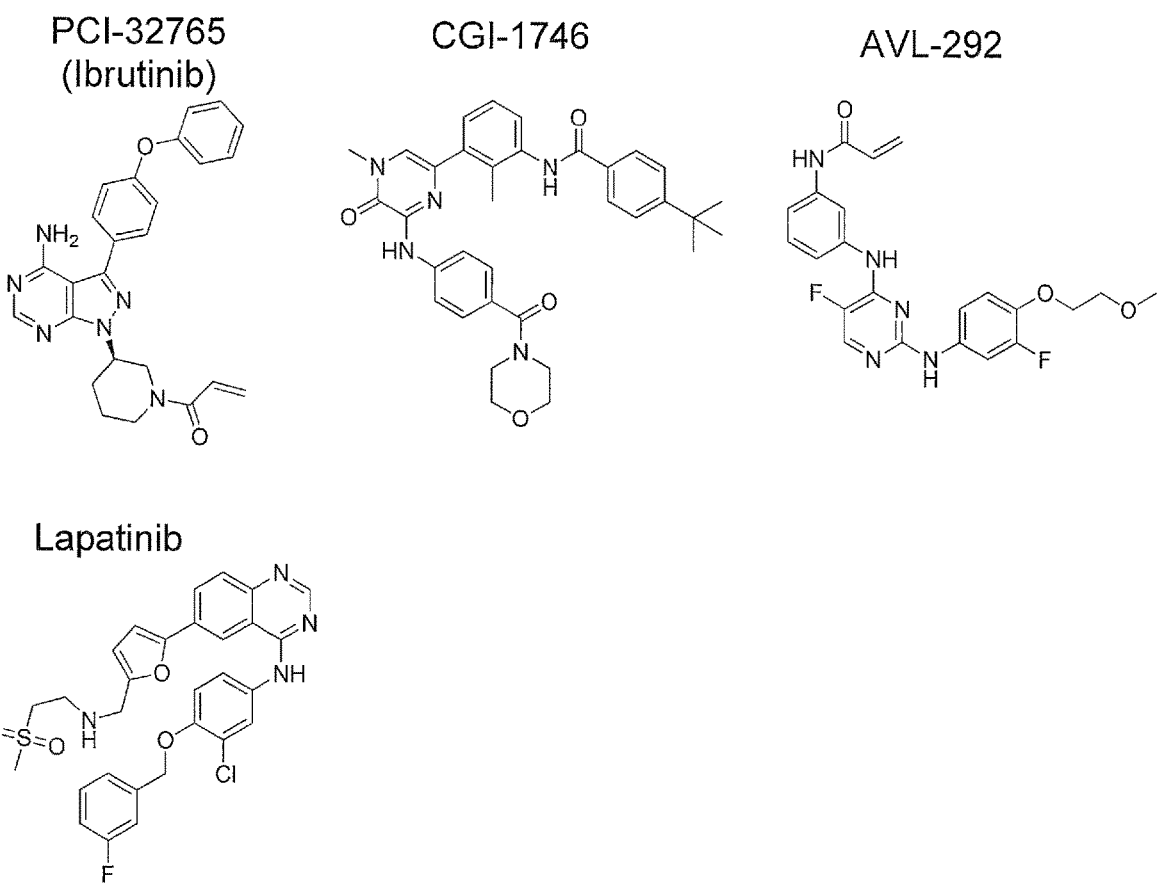
FIG. 8B shows the structures of PCI-32765 (Ibrutinib), CGI-1746, AVL-292, and lapatinib.
Figure 8C:
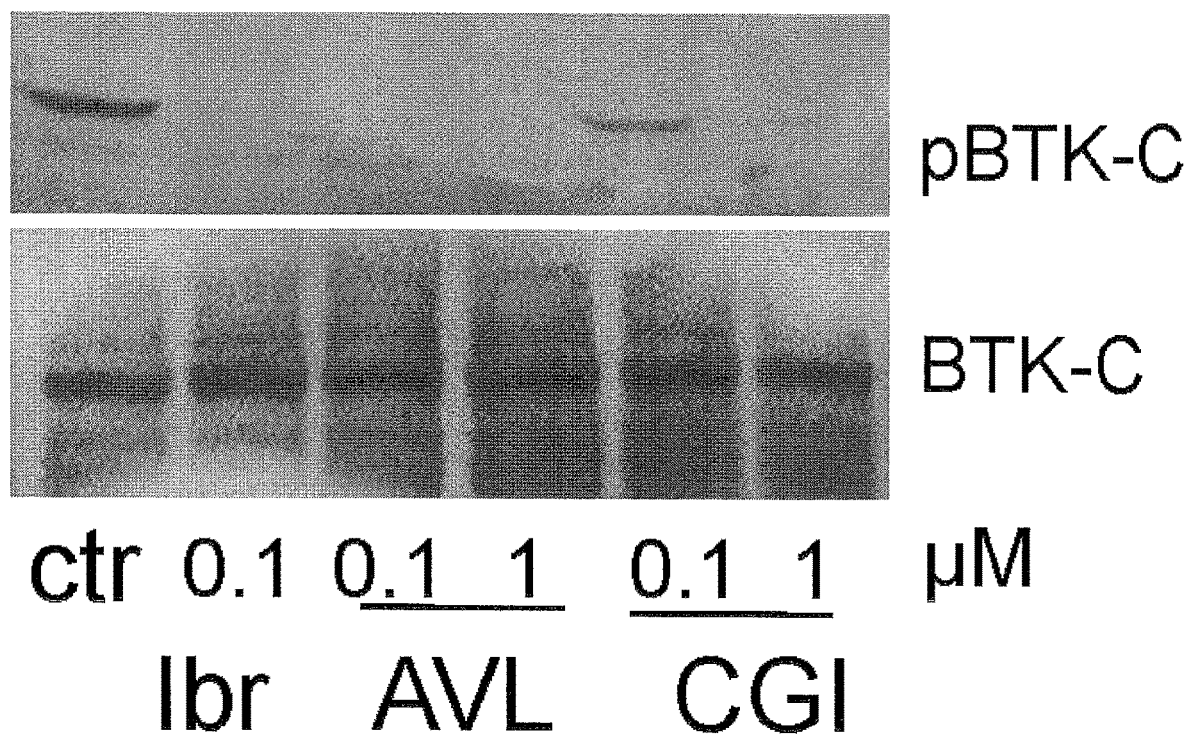
FIG. 8C shows that Ibrutinib and AVL-292 inhibit BTK-C activating phosphorylation and are potentially useful as prostate cancer therapies.

In a functional genomic screen, a novel BTK isoform has been identified as a gene whose expression protects breast cancer cells from apoptosis [38]. In addition to genetic evidence, the first generation. BTK inhibitor LFM-A13 was shown to increase apoptosis levels in breast cancer cells. The recently developed second generation BTK inhibitors, including ibrutinib, AVL-292 and CGI-1746, are more potent, more specific and more useful clinically compared to LFM-A13 [42-44]. In 2013, ibrutinib was approved by the FDA for treatment of B cell malignancies [45, 46]. As a first step in exploring the potential clinical utility of the second generation BTK inhibitors, cell growth assays were performed to determine the effect of these inhibitors on breast cancer cells. It was found that ibrutinib results in decreased cell number in breast cancer cells MCF7, SKBR3 and MDA-MB-231, but not in MCF-10A cells (FIG. 1A). These results are consistent with previous findings [38]. Surprisingly, it was observed that HER2-positive breast cancer cells SKBR3 are more sensitive to ibrutinib (1 μM), which reduces cell numbers by more than 80% at 3 days (FIG. 1). To extend these findings to another HER2-positive breast cancer cell, the effect of ibrutinib on BT474 cell survival were tested. The result shows that ibrutinib inhibits HER2-positive breast cancer cell growth at a concentration of 10 nanomolar (FIG. 1B). The IC50 for ibrutinib's effect on HER2-positive breast cancer cells measured at 3 days of culture is 0.03 μM. Also explored was whether HER2-positive breast cancer cells are sensitive to other BTK inhibitors. Although AVL-292 and CGI-1746 inhibit BTK-C kinase activity to the same degree as ibrutinib (FIG. 8A-C), they are less effective than ibrutinib causing a 30~40% decrease in cell numbers in HER2-positive breast cancer cell lines at higher concentrations (FIG. 1C). These results suggest that ibrutinib not only inhibits BTK-C activity, but also affects other targets specifically required for HER2-positive breast cancer cell survival.

Ibrutinib Effects in HER2-Positive Breast Cancer Cells

Figure 2A:
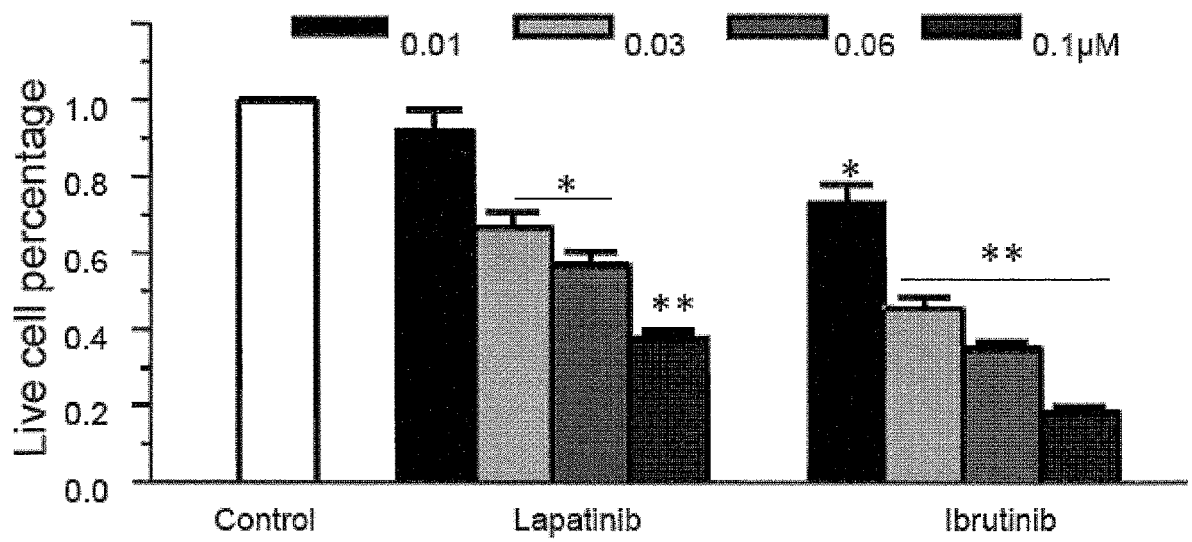
FIG. 2A-D shows the effect of lapatinib and ibrutinib on cell growth and signal transduction in BT474 cells.
Figure 2B:
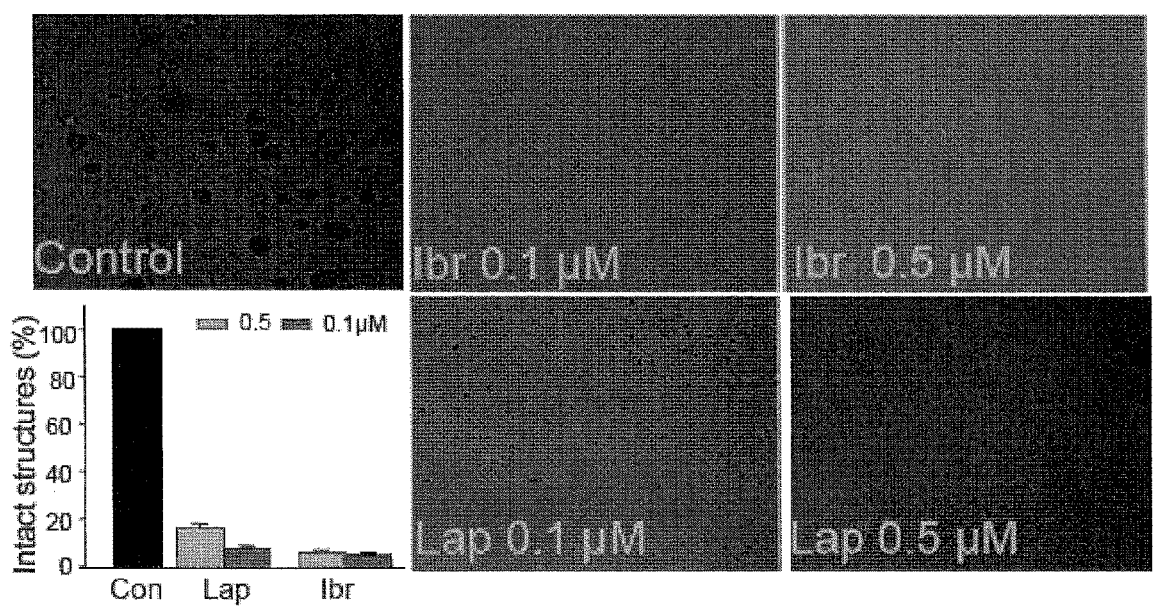

Ibrutinib is a covalent inhibitor of BTK [47] that irreversibly binds to a cysteine residue (Cys-481) near the ATP binding pocket of BTK. Sequence alignments show that only 10 kinases in the human genome have a cysteine residue at an analogous position. They include Blk, Btk, Bmx, EGFR, HER2, ErbB4, Itk, Jak3, Tec and Txk [48]. To compare the inhibitory effect of ibrutinib with lapatinib on HER2-positive breast cancer cells, their activity in monolayer culture was tested first. Lapatinib, a selective, reversible inhibitor of both EGFR and HER2 is currently used to treat HER2-positive breast cancer patients. Treatment with ibrutinib at different concentrations as indicated for 3 days reduces BT474 cell number. 0.01 μM of ibrutinib reduces cell populations to 30% of control ($p<0.01$). However, lapatinib, at the same concentration (0.01 μM) fails to reduce HER2-positive breast cancer cell numbers significantly (FIG. 2A). A number of studies have shown that cells' microenvironment can impact drug response [49, 50]. In order to test whether HER2-positive breast cancer cells are still sensitive to ibrutinib in 3D matrigel culture condition, treatment of BT474 cells with 0.1 μM or 0.5 μm of ibrutinib for 9 days significantly reduces cell number when compared with the control (FIG. 2B). Thus, it was found that ibrutinib reduces HER2-positive breast cancer cell number in both monolayer and 3D culture, and that ibrutinib has a more potent effect on HER2-positive breast cancer cells than lapatinib.

Figures 2C, 2D:
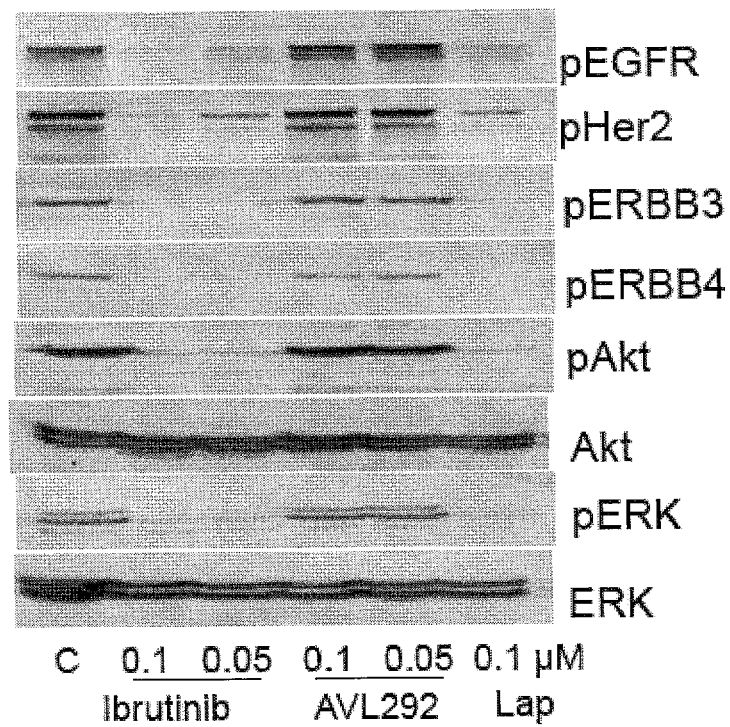

In HER2 overexpressing breast cancer cells, HER2 dimerizes with its partner EGFR or Her3. HER2/Her3 heterodimers directly phosphorylate the p85 regulatory subunit of PI3K activating the PI3K/Akt pathway [51]. In parallel, HER2/EGFR heterodimers also activate the MAPK pathway in most cases [52]. To examine the effect of ibrutinib on levels of activated Akt or Erk, BT474 cells was treated with 0.05 μM or 0.1 μM of ibrutinib and 0.1 μM of AVL-292 for 2 hours. It was found that ibrutinib inhibits the phosphorylation of EGFR, HER2, Her3 and ErbB4, which results in blocking downstream signaling that requires Akt or Erk activation. Compared with ibrutinib, AVL-292 does not block EGFR family signaling pathway activation, even though AVL-292 also covalently binds Cys481 on BTK. Lapatinib, a dual kinase inhibitor of EGFR and HER2, inhibits both AKT and ERK phosphorylation (FIG. 2D). These results suggest that ibrutinib also serves as a pan-EGFR family inhibitor and blocks the activation of each kinase, which leads to HER2-positive breast cancer cells more sensitive to ibrutinib.

Ibrutinib Effects on Proliferation of HER2-Positive Breast Cancer Cells.

Figure 3A:
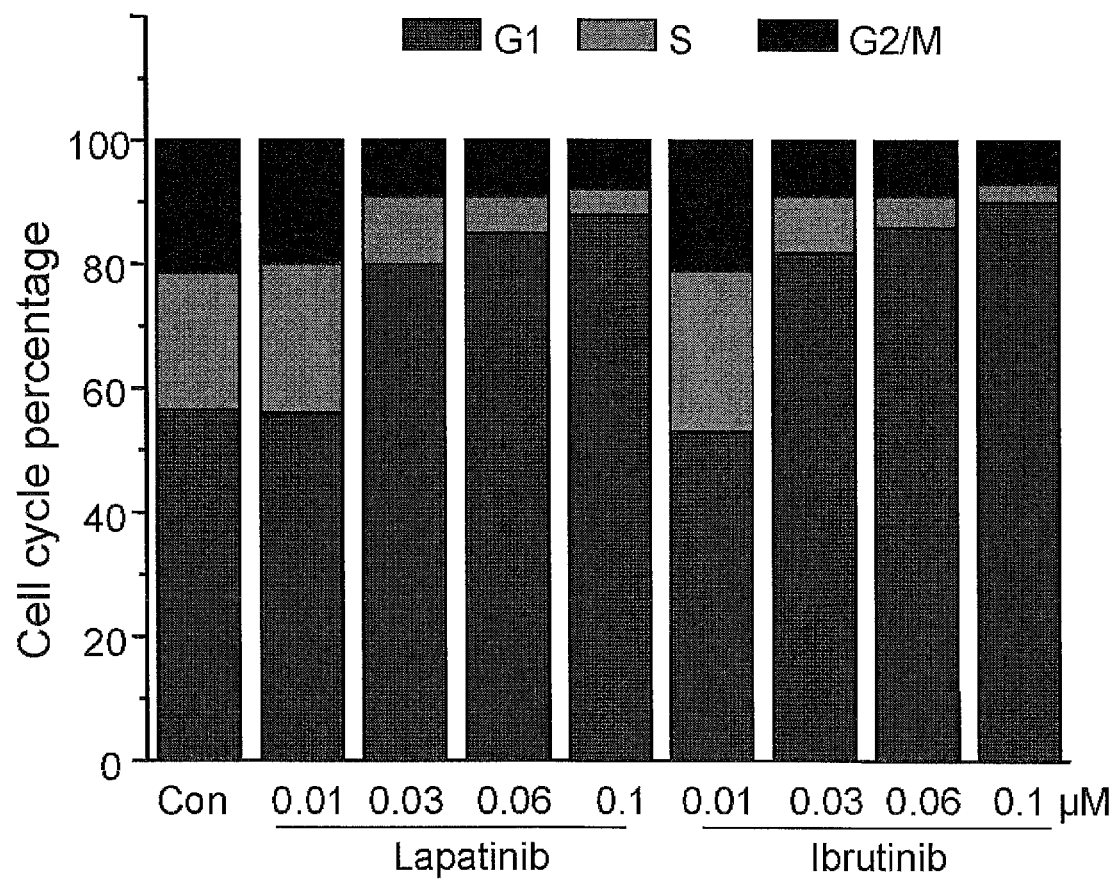
FIG. 3A-D shows the effect of ibrutinib on cell cycle and apoptosis.
Figure 3B:
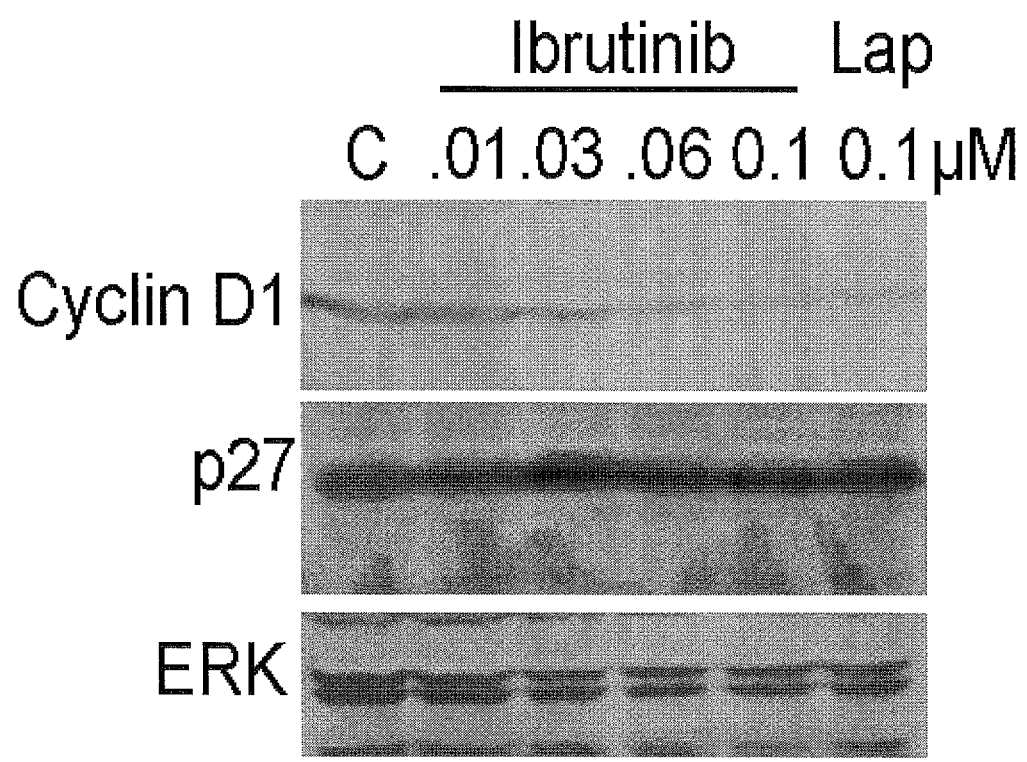

In HER2-positive breast cancer cells, the activation of HER2 stimulates both the MAPK and Akt signaling pathways, which results in cell proliferation due to increased G1-S phase transition and cell cycle progression [53]. Treatment of Her-2 overexpressing BT474 human breast cancer cells for 24 hours with ibrutinib or lapatinib leads to an appreciable G1-S arrest. A significant 50% decrease in the number of cells in the S phase of the cell cycle is observed at a concentration of 0.03 µM for ibrutinib when compared with controls (FIG. 3A). Similar results are seen for lapatinib[53]. This cell cycle delay is correlated with an increase in p27, an inhibitor of cell cycle progression, and a decrease in cyclin D1 (FIG. 3B).

Figure 3C:
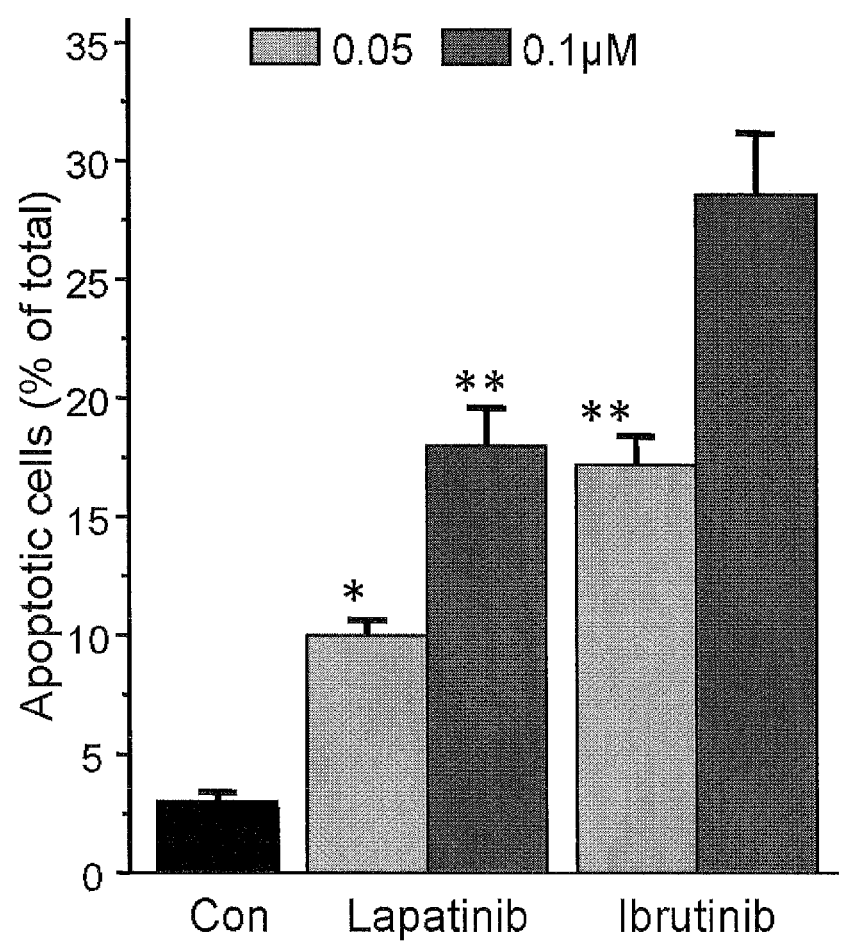
Figure 3D:
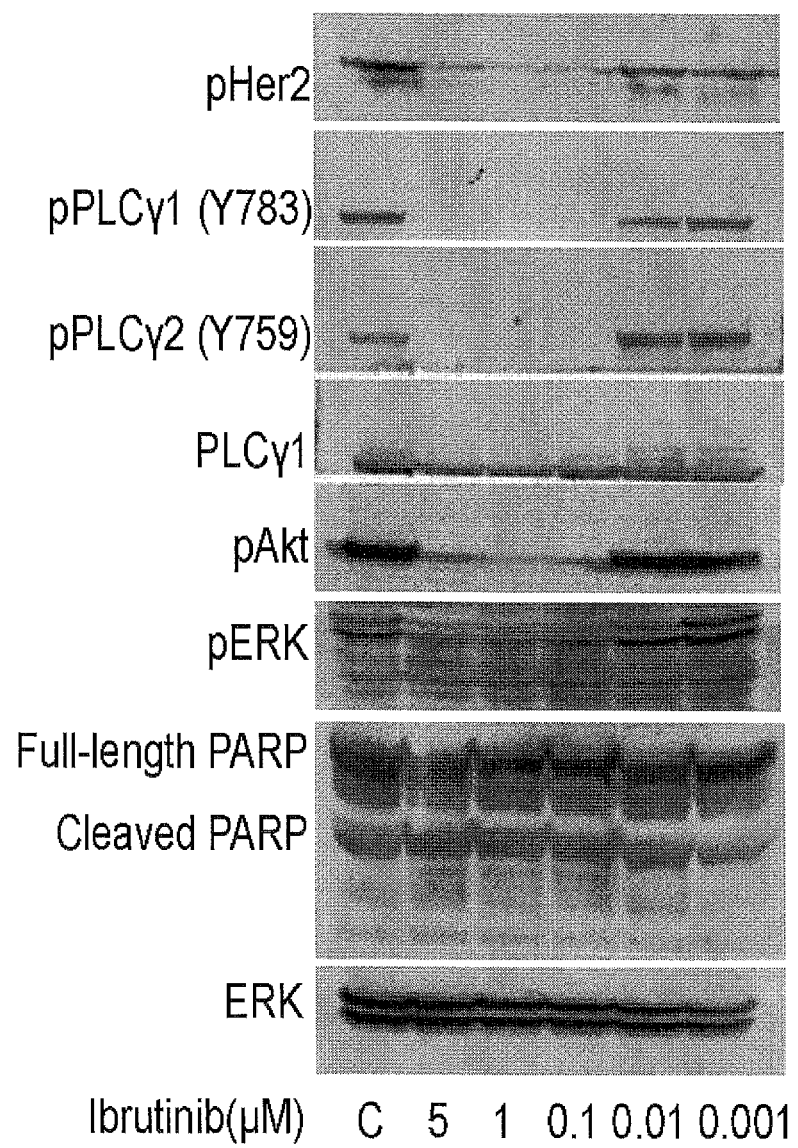

An increase in the number of apoptotic cells following treatment with 0.05 or 0.1 µM ibrutinib or lapatinib for 24 hours is observed. These results are consistent with the results of earlier studies, which have shown the effect of 0.1 or 0.5 µM lapatinib on cell survival [53]. Compared with lapatinib, ibrutinib induces apoptosis 1.5 fold in HER2-positive breast cancer cells (FIG. 3C). The effect of ibrutinib on cell survival regulatory proteins was also examined. Ibrutinib blocks PLCγ1, PLCγ2, Akt and ERK phosphorylation, and increases cleaved PARP (FIG. 3D). Taken together, these results suggest that ibrutinib decreases cell numbers by inducing both a G1-S delay and apoptosis in HER2-positive breast cancer cells.

Ibrutinib Blocks the Reactivation of AKT and ERK Pathways Induced by NRG1 or EGF in HER2-Positive Breast Cancer Cells.

Figure 4A:
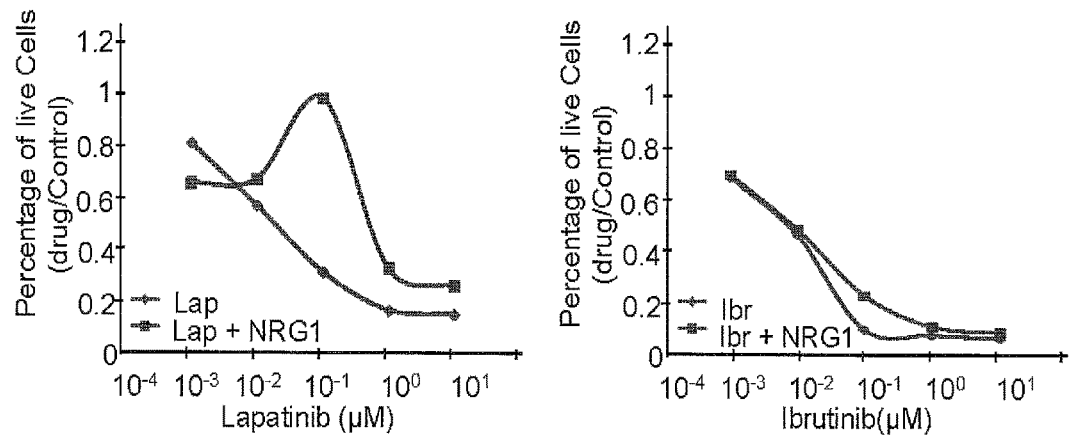
FIG. 4A-D shows inhibition pro-survival pathway re-activation by ibrutinib.

Cancer cells typically express multiple receptor tyrosine kinases (RTKs) which control cell survival signals [54]. RTK ligands are produced via autocrine tumor-cell production, paracrine tumor stroma production and systemic production [55]. An increase in RTK ligands has been shown to result in the resistance of cancer cells to RTK inhibitors [56]. In HER2-positive breast cancer cells, NRG1 is the most broadly active ligand, followed by EGF [57]. It was hypothesized that the greater efficacy of ibrutinib may impact the occurrence of growth factor dependent lapatinib resistance. The effect of exposing HER2-positive cells to 50 ng/ml of NRG1 with different concentration of lapatinib or ibrutinib was first tested for 3 days. The results again show that lapatinib or Ibrutinib potently suppresses cell growth. However, NRG1 application is able to rescue lapatinib-induced growth inhibition in HER2-positive breast cancer cells allowing resistant cells to emerge from the treatment (FIG. 4A). In contrast, HER2-positive breast cancer cells cannot be rescued from ibrutinib-induced growth inhibition by NRG1. Similar results are observed using 50 ng/ml of EGF.

Figure 4B:
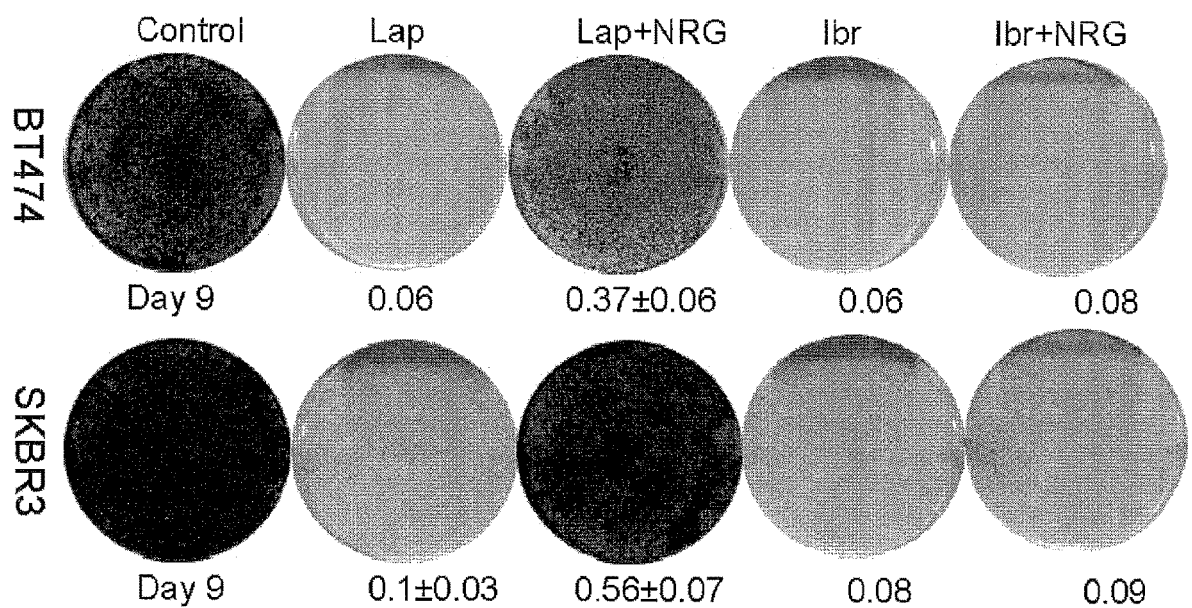
Figure 9A:
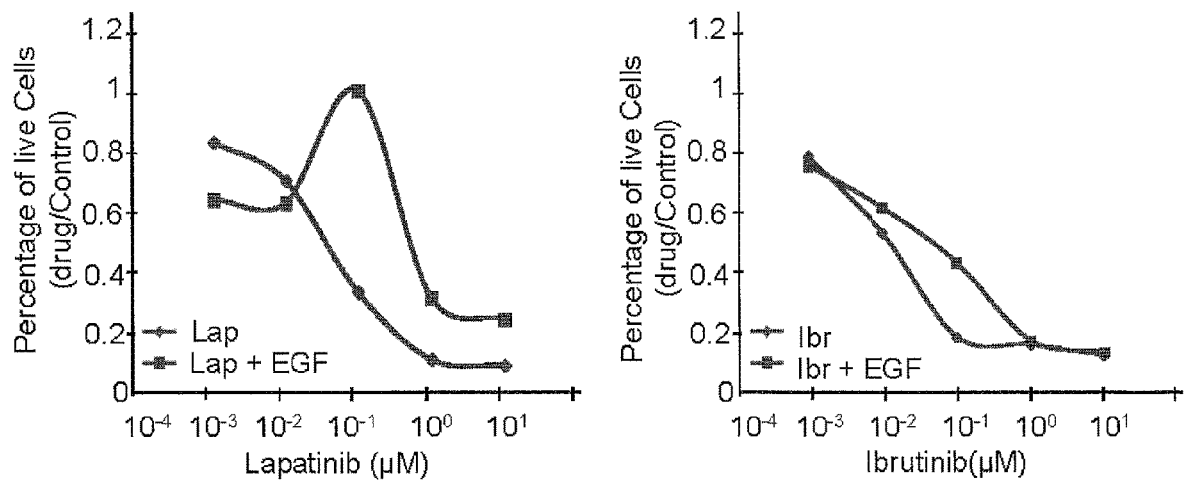
FIG. 9A shows an experiment using EGF where cells are co-treated with EGF/lapatinib or EGF/ibrutinib.
Figure 9B:
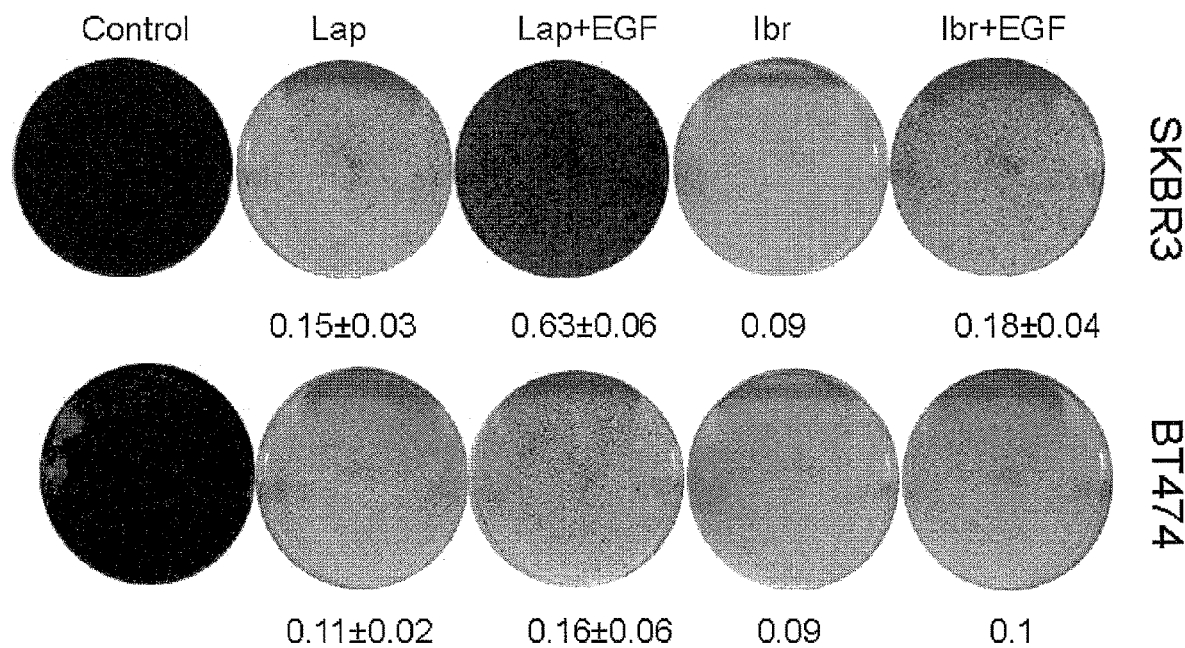
FIG. 9B shows an experiment using EGF where cells are co-treated with EGF/lapatinib or EGF/ibrutinib.

The ability of NRG1 or EGF signaling to rescue HER2-positive breast cancer cells from growth inhibition by HER2 kinase inhibitor lapatinib is consistent with other findings [56]. However, the findings that neither NRG1 nor EGF was able to rescue HER2-positive breast cancer cells from the growth inhibition by BTK inhibitor ibrutinib were unexpected. To further confirm these findings, additional long-term co-treatment experiments were performed. Nine days lapatinib/NRG1 co-treatment yields cells that exhibit lapatinib resistance in both BT474 and SKBR3 cell populations. In contrast, 9-days ibrutinib/NRG1 co-treatment does not yield ibrutinib resistant cells in HER2-positive breast cancer cell lines (FIG. 4B) Similar results are observed in experiments using EGF where cells are co-treated with EGF/lapatinib or EGF/ibrutinib (FIGS. 9A&B).

Figure 4C:
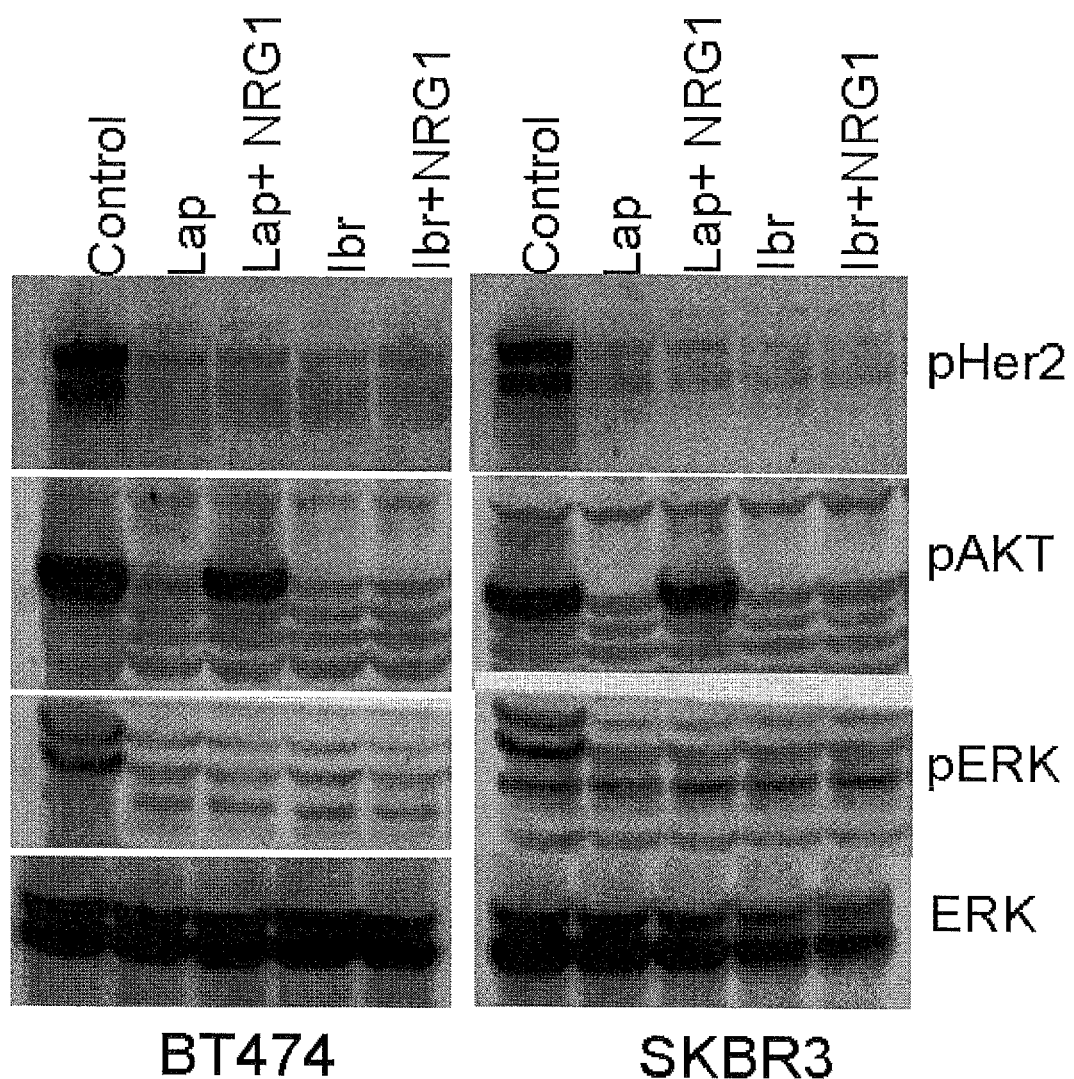

To investigate the signaling pathway which mediates the NRG1- or EGF-induced rescue of HER2-positive breast cancer cells, the activation of two downstream survival signaling pathways commonly engaged by RTKs was examined: the PI3K-AKT and MAPK pathway[57]. In the presence of lapatinib or ibrutinib alone, the activation of HER2, AKT and ERK are blocked. When cells are co-treated with NRG1/lapatinib, NRG1 re-activates AKT without activation of HER2. Surprisingly, NRG1 cannot re-activate AKT under conditions of NRG1/ibrutinib co-treatment (FIG. 4C). These results suggest that the NRG1 rescuing effect is blocked by ibrutinib which may target a second activated kinase. The results also suggest that lapatinib cannot block this second kinase.

Figure 4D:
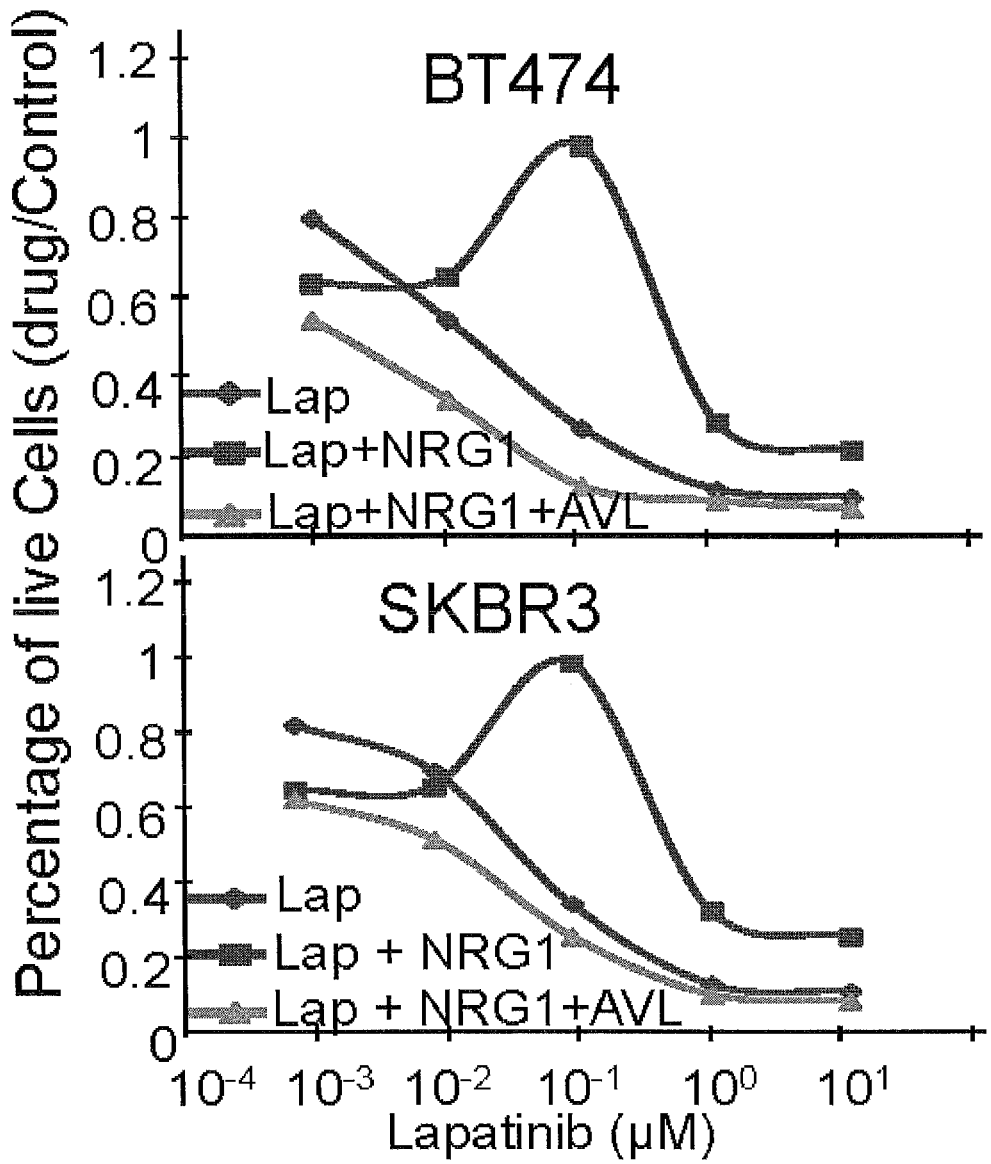

The above results showed that ibrutinib blocks the re-activation of AKT in HER2-positive breast cancer cells induced by NRG1, whereas lapatinib does not. Since ibrutinib was originally designed to block BTK activation and since BTK has been shown to activate AKT in B cells, the possibility existed that BTK-C provided a pro-survival signal in the genesis of lapatinib resistance. BTK-C was identified as a critical cell survival gene in a large scale RNAi screen in these cells was consistent with this notion. For these reasons, it was hypothesized that BTK-C mediated the re-activation of AKT induced by NRG1. However, since ibrutinib is as potent as an inhibitor of EGFR family activation as lapatinib in HER2-positive breast cancer cells, there was a need to dissociate the effects of EGFR inhibition from the effects of BTK inhibition. To test whether BTK-C is a secondary kinase that mediates NRG1 rescue in HER2-positive breast cancer cells, the BT474 and SKBR3 cells were treated with lapatinib, lapatinib/NRG1 or lapatinib/NRG1 plus AVL-292, a BTK inhibitor that does not inhibit the EGFR family (FIG. 2A-D). It was found that NRG1 rescue is blocked by simultaneously targeting BTK and the EGFR family when cells treated with lapatinib and AVL-292 (FIG. 4D). These results provide evidence that BTK-C signaling is involved in the appearance of ligand-dependent lapatinib resistance in treated HER2-positive breast cancer cell populations.

BTK-C Signaling in HER2-Positive Breast Cancer Cells

Figure 5A:
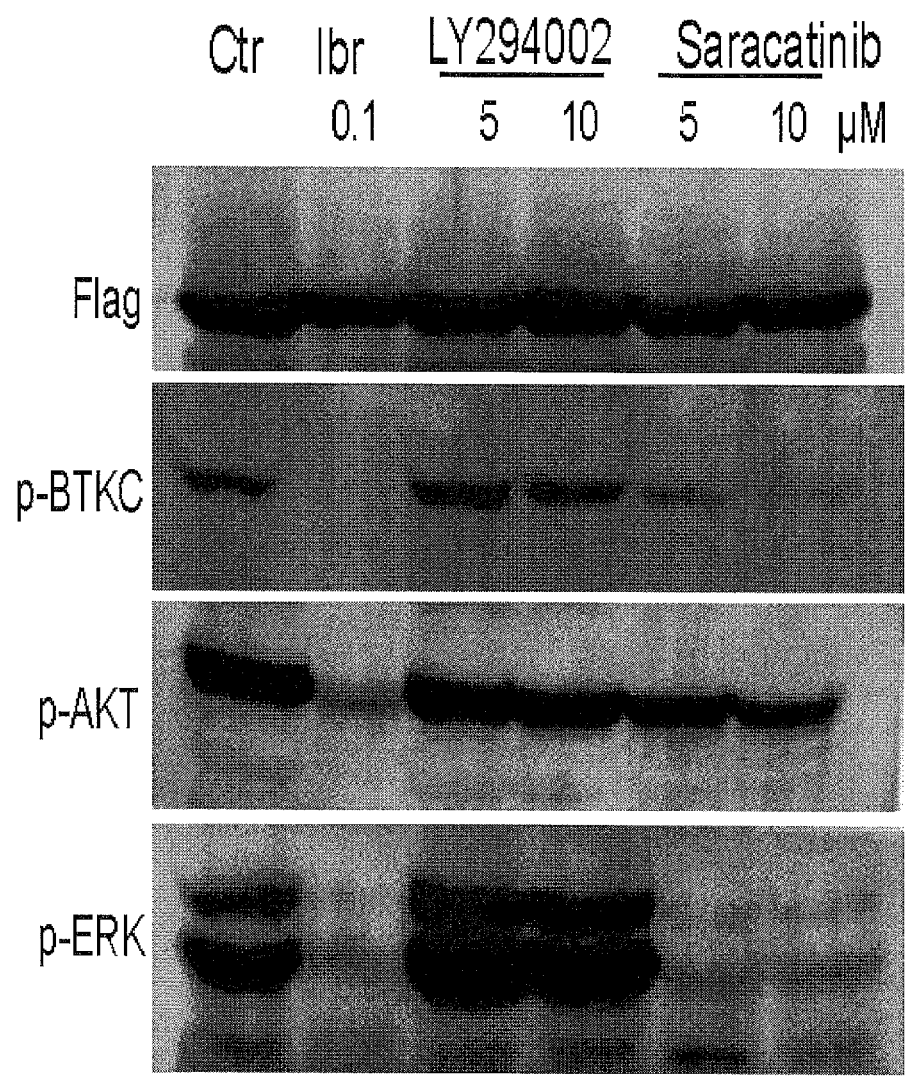
FIGS. 5A&B shows BTK-C activation by Src in breast cancer cells.
Figure 5B:
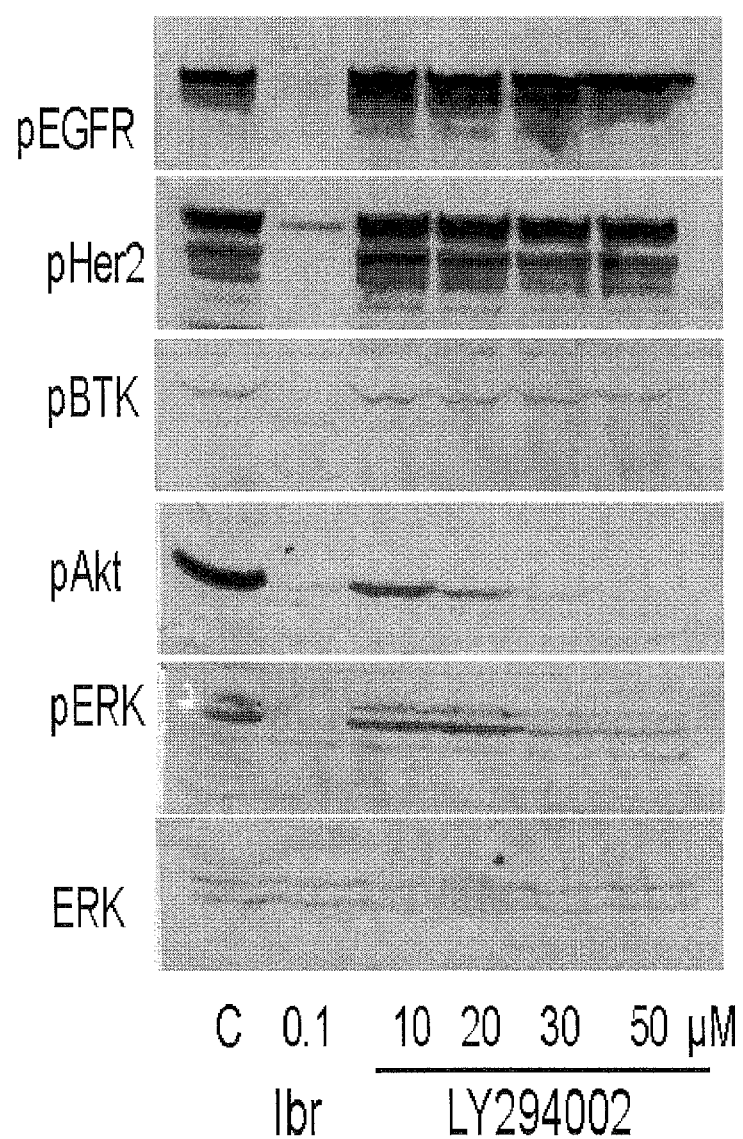
FIG. 5B shows SKBR3-btkc cells were treated with ibrutinib and different concentration of LY294002 for 24 h. Cell extraction were tested for phosphorylation of the indicated protein. Anti-ERK as a loading control.

The BTK signaling pathway has been extensively studied in hematopoietic cells. Upon antigen binding to the BCR, PI3K is activated. PI3K activity recruits BTK to the cell membrane through a PIP3-PH domain interaction, which allows SYK and LYN to fully activate BTK [58-60]. In previous studies, it was shown that a novel isoform of BTK (BTK-C) is expressed in human breast cancer cell lines and tissues. To explore the signaling activation of BTK-C in breast cancer cells, two potential upstream regulatory molecules of BTK-C: PI3K and Src were assessed [61]. First, the SKBR3-BTK-C cells were treated for 24 hours with established concentrations of PI3K inhibitor LY294002 (5 or 10 µM) or Src inhibitor Sarcatinib (5 or 10 µM). The phosphorylation of BTK-C is completely blocked by Sarcatinib at 10 µM [62]. The phosphorylation of AKT, as a downstream target of BTK-C, also decreases. In contrast, 10 µM of LY294002 does not suppress BTK-C activation (FIG. 5A). Since the possibility exists that this lower concentration of LY294002 may not block BTK-C activation, the concentration of LY294002 was increased to 50 µM and repeated the test. The results show that LY294002 at 50 µM completely blocks AKT activation, but not BTK-C activation (FIG. 5B). Collectively, these results suggest that Src, or a closely related kinase, is the main upstream molecule of the BTK-C activation signaling pathway in HER2-positive breast cancer cells. It also suggests that, due to the presence of an additional domain adjacent to the pleckstrin homology domain, the BTK-C isoform is not activated through PIP3 interaction as occurs with the B cell version of the kinase.

Figure 6A:
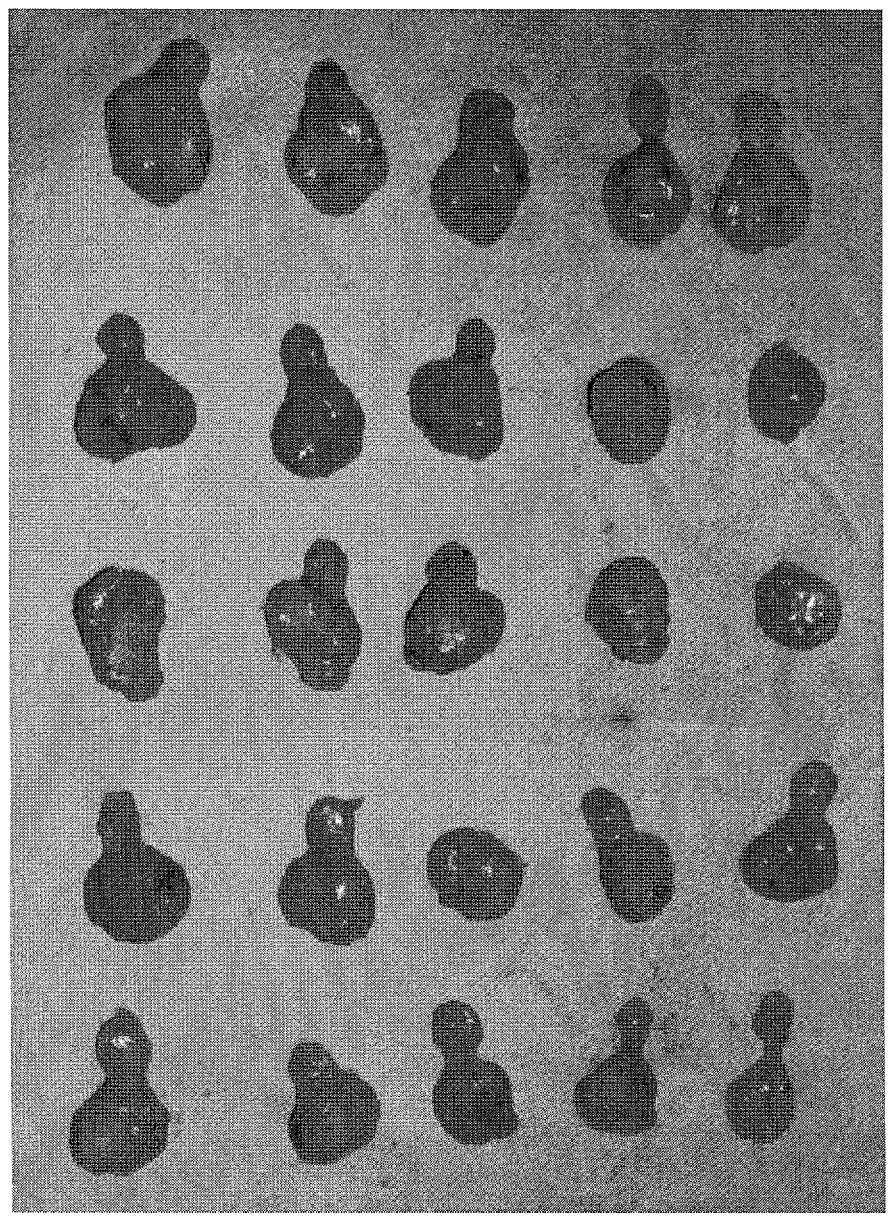
FIG. 6A-C show Ibrutinib inhibits Her2+ breast cancer cells growth in vivo.
Figure 6B:
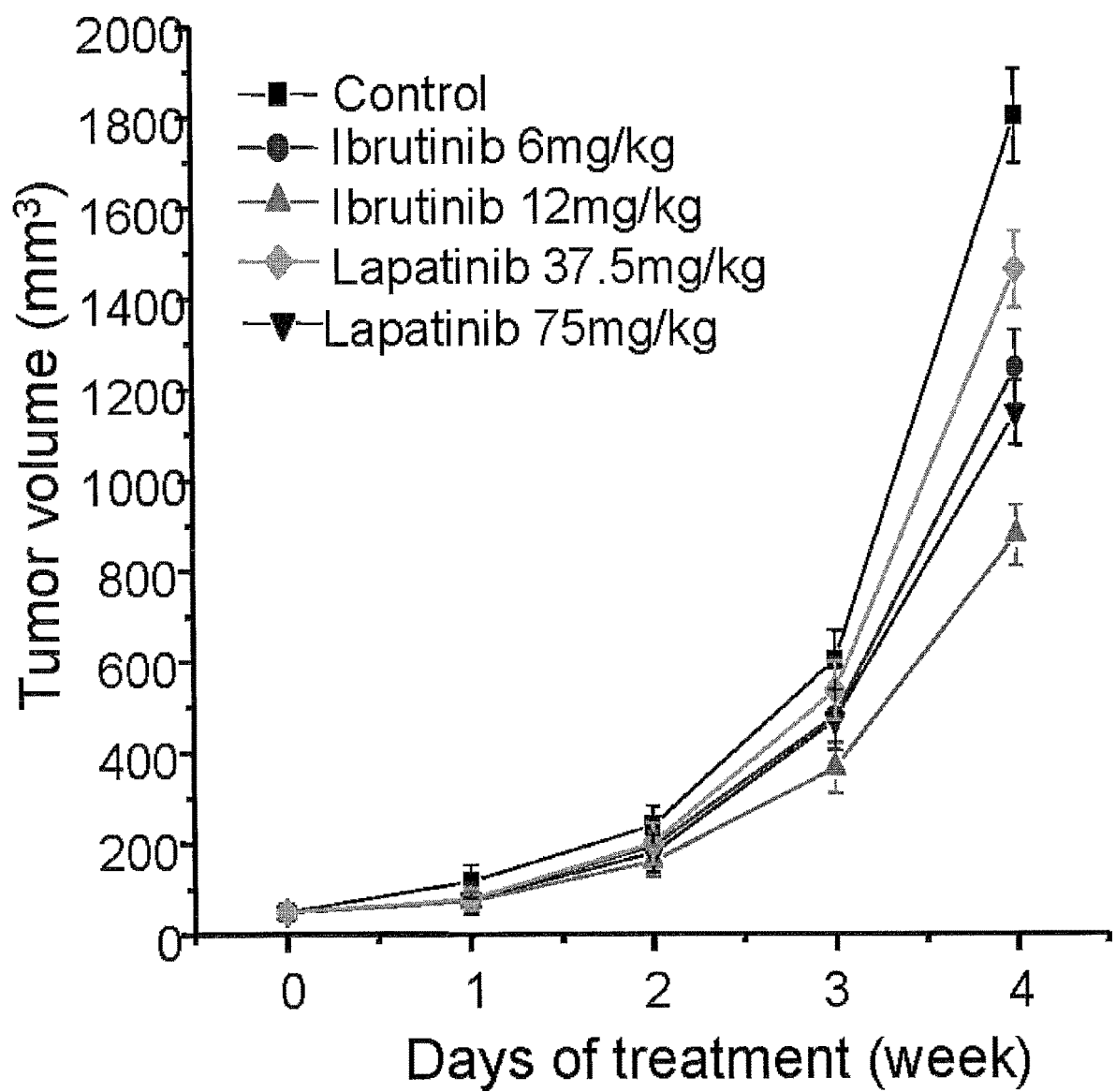
Figure 6C:
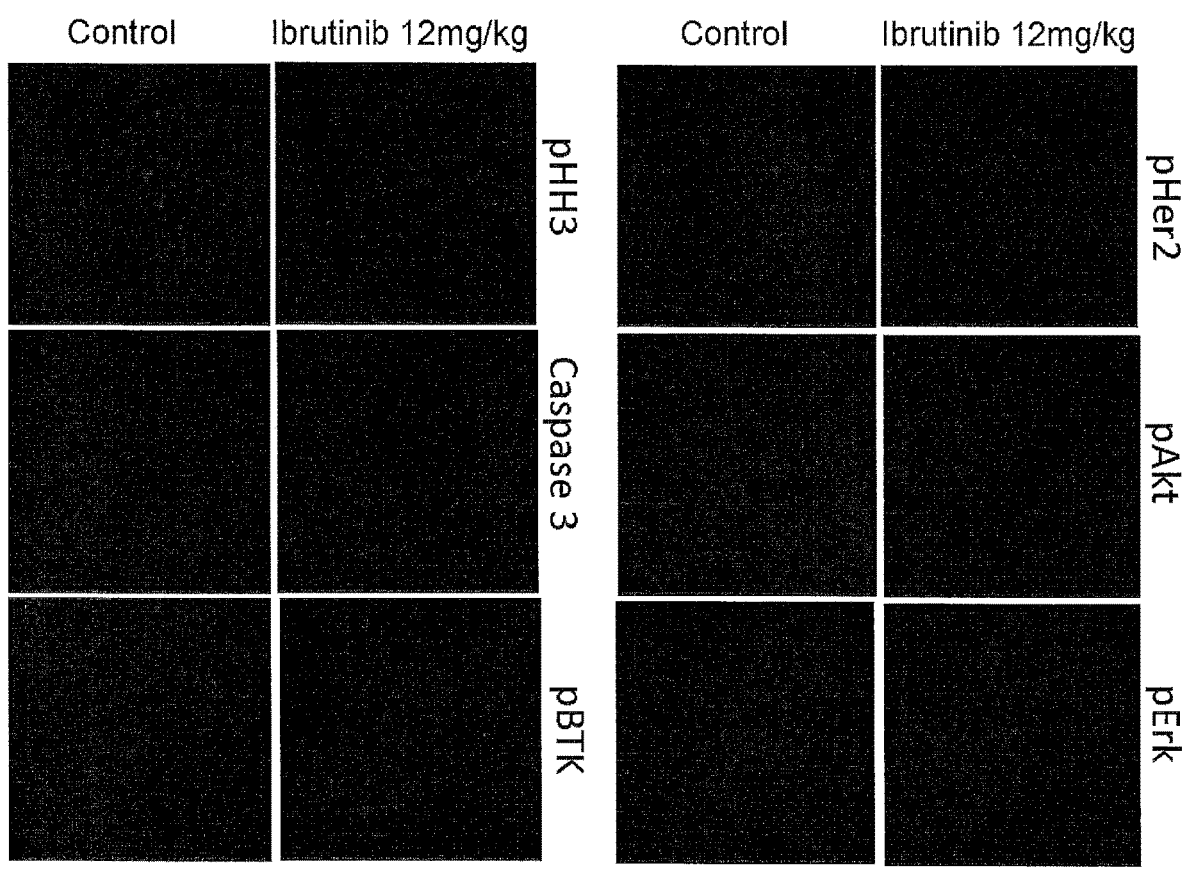

Effects of Ibrutinib Treatment on HER2-Positive Breast Tumor Xenografts Growth In Vivo These molecular experiments carried out in vitro pointed to the possibility that ibrutinib treatment might be useful in inhibiting Her2 positive tumor progression. To test this possibility, the effect of ibrutinib on xenografts of SKBR3 in NOD/SCID mice was assessed. Ibrutinib treatment inhibits tumor growth when administered to animals between 6 mg/kg/day and 12 mg/kg/day. At day 28, tumor volumes in mice that received 12 mg/kg are 45% smaller than the volumes in mice that receive a vehicle control (p<0.01)(FIG. 6A). To determine whether inhibition of tumor growth was correlated with inhibition of the target molecules, Her2 and BTK phosphorylation were examined in tumor tissues by immunofluorescence staining as well as downstream targets AKT and ERK phosphorylation. Phosphorylation of Her2, BTK, AKT and ERK are inhibited by ibrutinib treatment (FIG. 6B). In addition, changes in proliferation and apoptosis markers in tumor tissues reflect the effect that ibrutinib has in xenografts of SKBR3. The ability of ibrutinib to target both Her2 and BTK-C in these xenografts confirms the in vitro findings and provides a strong rationale for the use of ibrutinib in HER2-positive breast cancer chemotherapy.

The Expression of BTK-C in HER2-Positive Breast Cancer Tissue

Figures 7A, 7B:
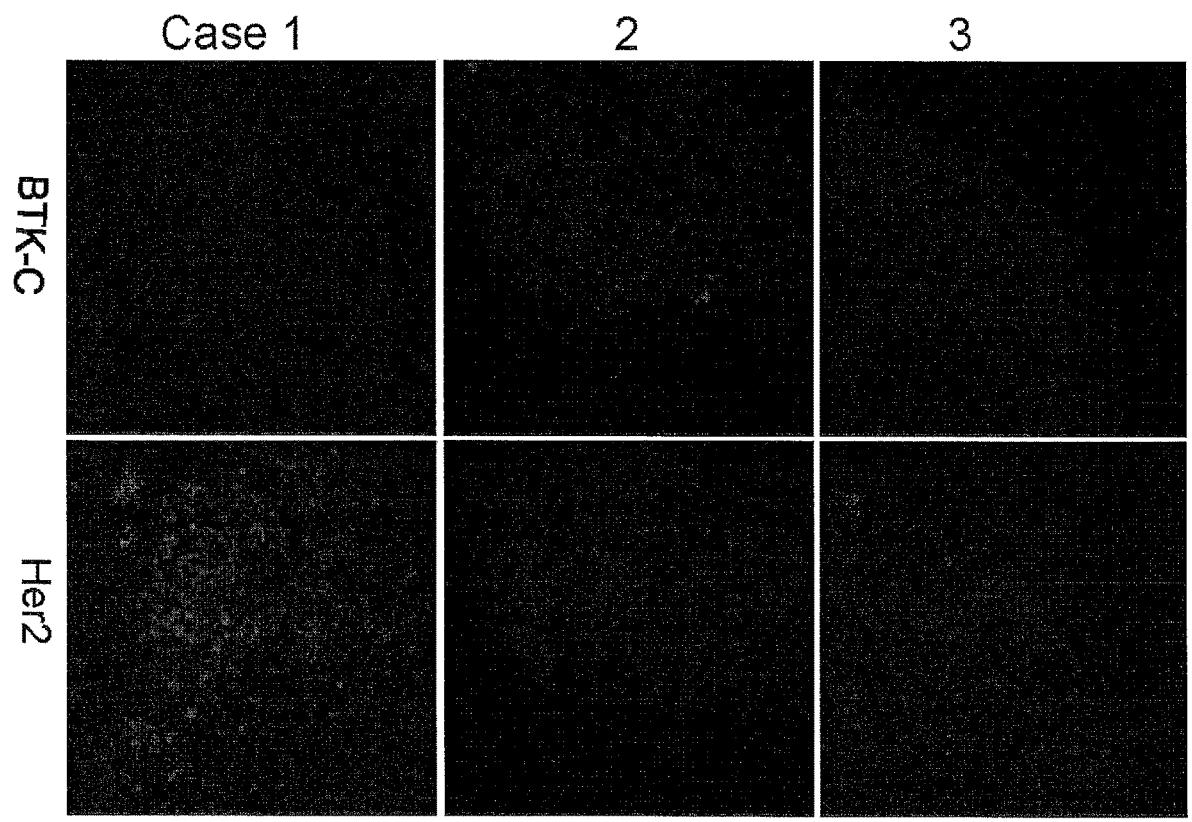
FIGS. 7A&B shows positive correlation between BTK and Her2 expression in surgical specimens of human breast cancer tissue.
FIG. 7B shows a summary of the positive correlation. The correlation between the overexpression of BTK-C and Her2 was analyzed by Fisher's exact test.

The above results suggest that simultaneously targeting HER2 and BTK represents an improved approach to the treatment of HER2-positive breast cancer. The BTK-C isoform was identified as a gene whose function is critical for breast cancer cell survival even though its expression levels are quite low. For this gene product to be a useful target, it is necessary to determine the frequency of its expression in HER2+ breast cancer. Although currently routine for many genes, establishing BTK-C expression patterns in tumors by querying available databases is not possible. The BTK-C isoform has only recently been described and little is understood regarding its expression. This is due in part to the fact that Affymetrix probes for this region have only been included in exon microarrays very recently. Additionally, the BTK-C isoform encodes the entire B-cell version sequence (BTK-A) and is annotated as a 5' UTR splice variant of BTK-A [38]. To provide further evidence about the expression of BTK-C on breast cancer tissues especially on HER2-positive breast cancer tissues, the co-expression of BTK-C and HER2 in surgical specimens of human breast cancer tumor tissues by immunofluorescence was examined. Again, it was found that BTK-C expresses in 30% of breast cancer tumor tissues (FIGS. 7A&B). Among 23 HER2-positive human breast cancer tissues, 43% are positive for BTK-C. There is a statistically significant association of expression of BTK-C with HER2 expression (p<0.01) (FIG. 7B). These findings strongly suggest that BTK-C and HER2 are positive correlation expression in human breast cancer tissues, and ibrutinib could be a new drug for treatment HER2 breast cancer by targeting BTK and HER2 simultaneously.

Discussion

Previous findings showed that a novel isoform of BTK (BTK-C) is frequently expressed in human breast cancer cells and tissues and that this isoform plays a crucial role in cell survival. Consistent with these findings, it was reported that several second generation BTK inhibitors reduce breast cancer cell number in a variety of cell types including MCF7, MDA-MB-231 and SKBR3 cells. Importantly, it was found that HER2-positive breast cancer cells are highly sensitive to ibrutinib. Ibrutinib, with an 1050 for these cells of 0.03 µM, is much better at decreasing cell numbers than the other BTK inhibitors, AVL-292 and CGI-1746, and compares favorably with lapatinib. In vitro, enzymatic activity assays show that 1050 of lapatinib for EGFR and HER2 are 10.8 and 9.2 nM respectively. These results indicate that the sensitivity of HER2-positive breast cancer cells to ibrutinib is due to the drug's ability to simultaneously suppress the activation of both BTK-C as well as the EGFR family. Consistent with previous studies, ibrutinib treatment results in induction of a pronounced G1/S delay and increased apoptosis in HER2-positive breast cancer cells [53]. It was also found that BTK-C plays an essential role in the ability of HER2-positive breast cancer cells to develop resistance to lapatinib under conditions when the growth factors NRG1 or EGF are present. NRG1 or EGF are unable to re-activate PI3K/Akt or MAPK signaling pathways and allow cells to escape the inhibitory effects of lapatinib when BTK-C is blocked by AVL-292, which is incapable of inhibiting the EGFR family. Since ibrutinib inhibits the activity of the EGFR family and inhibits the BTK-dependent reactivation of the PI3K/Akt or MAPK signaling pathways, it is a strong candidate to replace lapatinib as a combination therapy with trastuzumab for HER2-positive breast cancer patients who might otherwise develop resistance to lapatinib. As was found that the expression of BTK-C and HER2 are positively correlated in human breast cancer tissue with 40% of HER2-positive breast cancer tissues also being BTK-C positive, the potential utility of the drug is significant.

In accord with the in vitro studies, these results show that ibrutinib treatment at 12 mg/kg/day causes a significant 45% inhibition of Her2-positive tumor growth in vivo. Animals tolerate ibrutinib at this dose, although ibrutinib-related toxicity was observed. Consistent with ibrutinib's antitumor effects, staining of the proliferation marker, phosphorylated histone H3, decreased in treated xenografts tumor tissues compared with untreated control tumor tissues. Moreover, focal apoptotic lesions caused by ibrutinib treatment was observed, as evidenced by caspase 3 staining in xenografts tumor tissues. In these experiments, lapatinib treatment at 75 mg/kg/day was less potent in SKBR3 tumor xenograft models than ibrutinib treatment at 12 mg/kg/day. This is likely due to the ability of ibrutinib to target irreversibly both BTK and EGFR family members and block re-activation of PI3K/AKT or MAPK caused by growth factors such as NRG1 in vivo. Taken together, these findings show that ibrutinib actively blocks BTK and EGFR family activation efficiently inhibiting HER2-positive breast cancer growth in vivo. As a result, this study supports the use of ibrutinib as a HER2-positive breast cancer treatment and indicates that targeting BTK-C with second generation BTK inhibitors such as ibrutinib or AVL-292 may avert the development of drug resistance in breast cancer patients.

The advent of HER2-directed therapy has significantly improved the prognosis of patients with metastatic and early HER2-positive breast cancer. Currently, there are two classes of HER2-targeting drugs used in the clinic. Trastuzumab, Trastuzumab-DM1 and Pertuzumab are antibody based drugs, whereas lapatinib is a small molecule that reversibly inhibits both EGFR and HER2, blocking the PI3K/Akt and MAPK pathways. Lapatinib is the only small compound used to treat HER2-positive breast cancer that has metastasized to the brain due to its ability to cross the blood-brain barrier. Despite this recent progress, acquired resistance to HER2-directed therapy still results in relapse and progression of HER2-positive disease. The primary mechanism of resistance to lapatinib stems from increased levels of EGFR or HER3 ligands such as NRG1 or EGF in the tumor microenvironment which re-activate the PI3K/Akt and MAPK signaling pathways that are blocked by the drug [56]. The activation of the signaling pathway downstream of EGFR family members other than HER2 is dependent on heterodimerization of the EGFR family member triggered by NRG1 or EGF binding to the extracellular ligand-binding domain. Increased expression of HER2 at the cell membrane leads to constitutive signaling of downstream pathways: PI3K/Akt and the Ras/Raf/MEK/MAPK, which are involved in regulating cell growth, survival, differentiation, migration and metastasis. Reactivation of these pathways allows cells to escape from the anti-proliferative and anti-apoptotic effects of the HER2 inhibitors.

Ibrutinib was the first reported covalent inhibitor of BTK [48]. As an orally bioavailable, selective and irreversible inhibitor, ibrutinib has been undergoing multiple clinical trials targeting treatment of various B-cell malignancies and has shown promising clinical efficacy [47]. Based on sequence alignments, 10 kinases in the human genome have an orthologous cysteine residue [48]. The EGFR family includes EGFR/Her1, HER2, Her3 and Her4 all of which are involved in several aspects of tumorigenesis. These kinases include EGFR, HER2 and Her4 covalently bind to the thiol group of Cys481 in the ATP pocket region of BTK (position Cys515 of BTK-C). In vitro, enzymatic activity assays show that and have IC50 of ibrutinib for each enzyme in the nm range BTK, EGFR, HER2 and Her4 are 0.5, 5.6, 9.4 and 0.6 nM respectively. In addition, ibrutinib also inhibits ITK, an essential enzyme in Th2 T cells, which shifts the balance between Th1 and Th2 T cells and potentially enhances antitumor immune responses [63]. Given the relevance of this spectrum of targets, it is therefore not surprising that ibrutinib is effective in decreasing the proliferation and increasing apoptosis in HER2-positive breast cancer cells.

Based on BTK expression data, its function in breast cancer cells and ibrutinib's targets, it can predicted that ibrutinib, an irreversible BTK inhibitor, might be used in neoadjuvant or adjuvant setting with Trastuzumab or other chemotherapeutic compounds for HER2-positive breast cancer in the future. Moreover, ibrutinib abolishes the ability of either NRG1 or EGF to re-activate Akt or Erk in HER2-positive breast cancer cells. In vivo, ibrutinib blocks HER2-positive breast cancer cell xenograft growth. Finally, a strong correlation of the co-expression of BTK-C and HER2 in human breast cancer tissues was identified. This work demonstrates that BTK-C could be a novel therapeutic target for breast cancer, and that current second-generation BTK inhibitors could be used new drugs in HER targeted therapy for HER2-positive breast cancer patients.

Materials and Methods
Cell Culture and Chemicals.

Breast cancer cell lines and MCF-10A were obtained from American Type Culture Collection. All cell lines were cultures in DMEM (Hyclone) supplemented with 10% fetal bovine serum (FBS; Hyclone) and 100 units/μl of penicillin-streptomycin (Cellgro), except for MCF-10A cells cultured as indicated in. The BTK inhibitors Ibrutinib was purchased from ChemieTek, AVL-292 was purchased from MedKoo Biosciences, CGI-1764 was purchased from Axon Medchem. Recombinant human-β1 and Matrigel were purchased from R&D. Src inhibitor Saracatinib was purchased from Selleckchem. LY294002 was purchased from Cell Signaling.

Cell Viability Assays.

For live cell counts, cell growth on 96-well plates were fixed 4% formaldehyde and counterstained with Hoechst 33342 for nuclei. Images of cells were acquired using an In Cell Analyzer 1000 (GE Healthcare) high-content imaging system. At least 30 fields were imaged per well. Statistics were performed using the In Cell Investigator 3.4 image analysis software (GE Healthcare).

3D cell culture was performed as previously described [64]. The BT474 cells were propagated in DMEM with FBS. Single cells in medium containing 5% Matrigel were seeded at a density of $5 \times 10^4$ cells/cm$^2$ on a Matrigel-coated well. The top medium with 5% Matrigel and ibrutinib or lapatinib was changed every 3 days. Using 1 μM of ethidium bromide stains cell death during 3d culture.

Cells were cultured in 6-well plates for indicated days. Cells were fixed with 3.7% paraformaldehyde for 10 min and washed with PBS. After wash, cells were stained with 0.05% CV for 30 min Whole plate was washed with tape water. Dry plate was added with 0.5 ml methanol to solubilize the dye. Taking an aliquot to 96-well plate and reading CV stain with OD 540. Tumorospheres were counted under low magnification.

Cell Cycle Analysis

Cells were cultured in six-well plates and treated with vehicle, lapatinib or ibrutinib at the concentration as indicated for 16 hours. After trypsinized, cells were collected and washed with cold PBS. Cells were fixed with 70% ethanol, washed and stained with PI/Triton X-100 staining solution (0.1% triton X-100, 2 μg/ml PI and 0.2 mg/ml DNAse-free RNAse) for 30 min. Samples were analyzed by flow cytometry.

Immunofluorescence:

Human breast cancer tissue sections (BR10010b, US Biomax, Inc. MD) were baked for 1 h at 62° C., serial alcohol for rehydration and microwaved in 0.01M sodium citrate for 20 min for antigen retrieval. The sections were serum blocked for 30 min, incubated overnight at 4° C. with first antibodies in phosphate-buffered saline and subsequently with Cy5-labeled secondary antibodies for 60 min, nucleus were stained with Hoechst 33342. The stained sections were mounted with anti-fade solution for microscopy. The two by two tables for human data was analyzed by Fisher's Exact Test. Significance were determined by the alpha level of 0.05.

Immunoblotting

Immunoblotting was performed essentially as described previously. Equal amounts of proteins were used. Antibodies used were anti-EGFR (1:1000,), anti-HER2 (1:1000,), anti-ERBB3, ERBB4 antibody, anti-BTK, anti-AKT, ERIK, anti-PLCγ1, PLCγ2 and anti-PARP (1:1000, cell signaling), anti-Flag antibody (1:1000, Sigma), anti-rabbit IgG-HRP and mouse IgG-HRP (1:5000, Jackson ImmunoResearch) [65].

Apoptosis Assay

Apoptotic cells were assessed with Alexa Fluor 488 annexin V apoptosis Kit (Invitrogen). Cells were treated with lapatinib of ibrutinib for 24 hours. Cells were trypsinized and washed with cold PBS and resuspend the cells in 1×annexin-binding buffer to $1 \times 10^6$ cells/ml. Add 5 μl Alexa Fluro 488 annexin V and 1 μl 100 μg/ml PI to each 100 μl of cell suspension. Incubate the cells for 15 min at room temperature. After the incubation, add 400 μl 1×annexin-binding buffer, mix gently and keep the sample on ice.

Samples were analyzed on a BD LSR II Flow Cytometer (BD Biosciences, San Jose, Calif.). The data were analyzed using the FlowJo software package (Treestar Inc., Ashland, Oreg.).

Animal Experiments

NOD/SCID mice were purchased from Jackson Lab (The Jackson Laboratory, Bar Harbor, Me., USA). All mouse procedures were approved by the Animal Care and Use Committees of SUNY Albany and performed in accordance with institutional policies.

For xenograft tumor studies, $1 \times 10^6$ SKBR3 cells were suspended in 50 µl Matrigel (BD Biosciences) diluted 1:2 with DMEM and injected into mammary fat pad. Treatment began when tumors were palpable. Ibrutinib was given p.o. 6 mg/kg/day or 12 mg·kg·day in a vehicle of 1% DMSO/30% polyethylene glycol/1% Tween 80. Lapatinib was given p.o. 75 mg/kg/day or 37.5 mg/kg/day. The tumor volume in $mm^3$ is calculated by the formula: volume=(width)$^2$×length/2 every 7 days.

Thus, specific compositions and methods of bruton's tyrosine kinase inhibitors have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Blume-Jensen, P. and Hunter, T. (2001) "Oncogenic Kinase Signalling," *Nature* 411(6835), 355-365.
2. Chu, D. and Lu, J. (2008) "Novel Therapies in Breast Cancer: What Is New from Asco 2008," *J. Hematol. Oncol. J Hematol Oncol* 1(1), 1-13.
3. Sabbah, M. et al. (2008) "Molecular Signature and Therapeutic Perspective of the Epithelial-to-Mesenchymal Transitions in Epithelial Cancers," *Drug Resist. Updat.* 11(4-5), 123-151.
4. Nahta, R. and Esteva, F. (2006) "Her2 Therapy: Molecular Mechanisms of Trastuzumab Resistance," *Breast Cancer Res.* 8(6), 1-8.
5. MacKeigan, J. P. et al. (2005) "Sensitized RNAi Screen of Human Kinases and Phosphatases Identifies New Regulators of Apoptosis and Chemoresistance," *Nat. Cell Biol.* 7(6), 591-600.
6. Call, J. A. et al. (2008) "Targeted Manipulation of Apoptosis in Cancer Treatment," *Lancet Oncol.* 9(10), 1002-1011.
7. Anderson, M. L. M. and Young, B. D. (1985) "Quantitative Filter Hybridization," in *Nucleic Acid Hybridisation: A Practical Approach* (Hames, B. D. and Higgins, S. J., Eds.), pp 73-111, Oxford University Press, USA.
8. Smith, T. F. and Waterman, M. S. (1981) "Comparison of Biosequences," *Adv. Appl. Math.* 2(4), 482-489.
9. Needleman, S. B. and Wunsch, C. D. (1970) "A General Method Applicable to the Search for Similarities in the Amino Acid Sequence of Two Proteins," *J. Mol. Biol.* 48(3), 443-453.
10. Pearson, W. R. and Lipman, D. J. (1988) "Improved Tools for Biological Sequence Comparison," *P.N.A.S.* 85(8), 2444-2448.
11. Mullis, K. B. et al. "Process for Amplifying, Detecting, and/or-Cloning Nucleic Acid Sequences," U.S. Pat. No. 4,683,195, application Ser. No. 06/828,144, filed Feb. 7, 1986. (issued Jul. 28, 1987).
12. Mullis, K. B. "Process for Amplifying Nucleic Acid Sequences," U.S. Pat. No. 4,683,202, application Ser. No. 06/791,308, filed Oct. 25, 1985. (issued Jul. 28, 1987).
13. Mullis, K. B. et al. "Process for Amplifying, Detecting, and/or Cloning Nucleic Acid Sequences Using a Thermostable Enzyme," U.S. Pat. No. 4,965,188, application Ser. No. 07/063,647, filed Jun. 17, 1987. (issued Oct. 23, 1990).
14. Sambrook, J. et al. (1989) "Synthesis of Single-Stranded RNA Proves by in Vitro Transcription," in *Molecular Cloning: A Laboratory Manual* (Sambrook, J., et al., Eds.) 2nd ed., pp 9.31-.58, Cold Spring Harbor Laboratory Press, New York.
15. Sambrook, J. et al. (1989) "Transfer and Fixation of Denatured RNA to Membranes," in *Molecular Cloning: A Laboratory Manual* (Sambrook, J., et al., Eds.) 2nd ed., pp 7.39-.52, Cold Spring Harbor Laboratory Press, New York.
16. Carthew, R. W. (2001) "Gene Silencing by Double-Stranded RNA," *Curr. Opin. Cell Biol.* 13(2), 244-248.
17. (2000) "Cancer Multidrug Resistance," *Nat. Biotechnol.* 18, IT18-IT20.
18. Gillet, J. P. and Gottesman, M. M. (2010) "Mechanisms of Multidrug Resistance in Cancer," *Methods Mol. Biol.* 596, 47-76.
19. Smith, L. et al. (2006) "The Analysis of Doxorubicin Resistance in Human Breast Cancer Cells Using Antibody Microarrays," *Mol. Cancer Ther.* 5(8), 2115-2120.
20. Farquhar, D. et al. (1991) "Doxorubicin Analogs Incorporating Chemically Reactive Substituents," *J. Med. Chem.* 34(2), 561-564.
21. Giamas, G. et al. (2010) "Kinases as Targets in the Treatment of Solid Tumors," *Cell. Signal.* 22(7), 984-1002.
22. Baselga, J. (2006) "Targeting Tyrosine Kinases in Cancer: The Second Wave," *Science* 312(5777), 1175-1178.
23. Krause, D. S. and Van Etten, R. A. (2005) "Tyrosine Kinases as Targets for Cancer Therapy," *N. Engl. J. Med.* 353(2), 172-187.
24. Vassilev, A. O. and Uckun, F. M. (2004) "Therapeutic Potential of Inhibiting Bruton's Tyrosine Kinase, (Btk)," *Curr. Pharm. Des.* 10(15), 1757-1766.
25. Kris, M. G. et al. (2003) "Efficacy of Gefitinib, an Inhibitor of the Epidermal Growth Factor Receptor Tyrosine Kinase, in Symptomatic Patients with Non-Small Cell Lung Cancer: A Randomized Trial," *JAMA* 290(16), 2149-2158.
26. Shepard, H. M. et al. (2008) "Signal Integration: A Framework for Understanding the Efficacy of Therapeutics Targeting the Human Egfr Family," *J. Clin. Invest.* 118(11), 3574-3581.

27. Smith, C. I. et al. (2001) "The Tec Family of Cytoplasmic Tyrosine Kinases: Mammalian Btk, Bmx, Itk, Tec, Txk and Homologs in Other Species," *BioEssays* 23(5), 436-446.
28. Tsukada, S. et al. (1993) "Deficient Expression of a B Cell Cytoplasmic Tyrosine Kinase in Human X-Linked Agammaglobulinemia," *Cell* 72(2), 279-290.
29. Vetrie, D. et al. (1993) "The Gene Involved in X-Linked Agammaglobulinaemia Is a Member of the Src Family of Protein-Tyrosine Kinases," *Nature* 361(6409), 226-233.
30. Mohamed, A. J. et al. (2009) "Bruton's Tyrosine Kinase (Btk): Function, Regulation, and Transformation with Special Emphasis on the Ph Domain," *Immunol. Rev* 228(1), 58-73.
31. Aoki, Y. et al. (1994) "Bruton Tyrosine Kinase Is Tyrosine Phosphorylated and Activated in Pre-B Lymphocytes and Receptor-Ligated B Cells," *Proc. Natl. Acad. Sci. U.S.A* 91(22), 10606-10609.
32. Khan, W. N. et al. (1995) "Defective B Cell Development and Function in Btk-Deficient Mice," *Immunity* 3(3), 283-299.
33. Kawakami, Y. et al. (1994) "Tyrosine Phosphorylation and Activation of Bruton Tyrosine Kinase Upon Fc Epsilon Ri Cross-Linking," *Mol. Cell. Biol.* 14(8), 5108-5113.
34. Hendriks, R. W. et al. (2014) "Targeting Bruton's Tyrosine Kinase in B Cell Malignancies," *Nat. Rev. Cancer* 14(4), 219-232.
35. Buggy, J. J. and Elias, L. (2012) "Bruton Tyrosine Kinase (Btk) and Its Role in B-Cell Malignancy," *Int. Rev. Immunol.* 31(2), 119-132.
36. Vassilev, A. O. and Uckun, F. M. (2004) "Therapeutic Potential of Inhibiting Bruton's Tyrosine Kinase, (Btk)," *Current pharmaceutical design* 10(15), 1757-1766.
37. Kim, E. S. and Dhillon, S. (2015) "Ibrutinib: A Review of Its Use in Patients with Mantle Cell Lymphoma or Chronic Lymphocytic Leukaemia," *Drugs* 75(7), 769-776.
38. Eifert, C. et al. (2013) "A Novel Isoform of the B Cell Tyrosine Kinase Btk Protects Breast Cancer Cells from Apoptosis," *Genes, Chromosomes & Cancer* 52(10), 961-975.
39. Brown-Glaberman, U. et al. (2014) "Her2-Targeted Therapy for Early-Stage Breast Cancer: A Comprehensive Review," *Oncology* 28(4), 281-289.
40. De Placido, S. and Pronzato, P. (2015) "Treatment Options in Hr(+)/Her2(−) Advanced Breast Cancer Patients Pretreated with Nonsteroidal Aromatase Inhibitors: What Does Current Evidence Tell Us?," *Future Oncol.* 11(6), 1-7.
41. Figueroa-Magalhaes, M. C. et al. (2014) "Treatment of Her2-Positive Breast Cancer," *Breast* 23(2), 128-136.
42. Herman, S. E. et al. (2011) "Bruton Tyrosine Kinase Represents a Promising Therapeutic Target for Treatment of Chronic Lymphocytic Leukemia and Is Effectively Targeted by Pci-32765," *Blood* 117(23), 6287-6296.
43. Burger, J. A. (2014) "Bruton's Tyrosine Kinase (Btk) Inhibitors in Clinical Trials," *Curr. Hematol. Malig. Rep.* 9(1), 44-49.
44. Di Paolo, J. A. et al. (2011) "Specific Btk Inhibition Suppresses B Cell- and Myeloid Cell-Mediated Arthritis," *Nat. Chem. Biol.* 7(1), 41-50.
45. Byrd, J. C. et al. (2013) "Targeting Btk with Ibrutinib in Relapsed Chronic Lymphocytic Leukemia," *N. Engl. J. Med.* 369(1), 32-42.
46. O'Brien, S. et al. (2014) "Ibrutinib as Initial Therapy for Elderly Patients with Chronic Lymphocytic Leukaemia or Small Lymphocytic Lymphoma: An Open-Label, Multicentre, Phase 1b/2 Trial," *Lancet Oncol.* 15(1), 48-58.
47. Honigberg, L. A. et al. (2010) "The Bruton Tyrosine Kinase Inhibitor Pci-32765 Blocks B-Cell Activation and Is Efficacious in Models of Autoimmune Disease and B-Cell Malignancy," *Proceedings of the National Academy of Sciences of the United States of America* 107(29), 13075-13080.
48. Pan, Z. et al. (2007) "Discovery of Selective Irreversible Inhibitors for Bruton's Tyrosine Kinase," *ChemMedChem* 2(1), 58-61.
49. Lovitt, C. J. et al. (2015) "Evaluation of Chemotherapeutics in a Three-Dimensional Breast Cancer Model," *J. Cancer Res. Clin. Oncol.* 141(5), 951-959.
50. Weigelt, B. et al. (2010) "Her2 Signaling Pathway Activation and Response of Breast Cancer Cells to Her2-Targeting Agents Is Dependent Strongly on the 3d Microenvironment," *Breast Cancer Res. Treat.* 122(1), 35-43.
51. Eroglu, Z. et al. (2014) "Human Epidermal Growth Factor Receptor Family-Targeted Therapies in the Treatment of Her2-Overexpressing Breast Cancer," *Oncologist* 19(2), 135-150.
52. Rabindran, S. K. et al. (2004) "Antitumor Activity of Hki-272, an Orally Active, Irreversible Inhibitor of the Her-2 Tyrosine Kinase," *Cancer Res.* 64(11), 3958-3965.
53. Konecny, G. E. et al. (2006) "Activity of the Dual Kinase Inhibitor Lapatinib (Gw572016) against Her-2-Overexpressing and Trastuzumab-Treated Breast Cancer Cells," *Cancer Res.* 66(3), 1630-1639.
54. Moritz, A. et al. (2010) "Akt-Rsk-S6 Kinase Signaling Networks Activated by Oncogenic Receptor Tyrosine Kinases," *Sci. Signal.* 3(136), ra64.
55. Zhang, W. and Huang, P. (2011) "Cancer-Stromal Interactions: Role in Cell Survival, Metabolism and Drug Sensitivity," *Cancer Biology & Therapy* 11(2), 150-156.
56. Wilson, T. R. et al. (2012) "Widespread Potential for Growth-Factor-Driven Resistance to Anticancer Kinase Inhibitors," *Nature* 487(7408), 505-509.
57. Grant, S. et al. (2002) "Roles of Erbb Family Receptor Tyrosine Kinases, and Downstream Signaling Pathways, in the Control of Cell Growth and Survival," *Front. Biosci* 7, d376-389.
58. Rolli, V. et al. (2002) "Amplification of B Cell Antigen Receptor Signaling by a Syk/Itam Positive Feedback Loop," *Mol. Cell* 10(5), 1057-1069.
59. Saito, K. et al. (2001) "Interaction between the Btk Ph Domain and Phosphatidylinositol-3,4,5-Trisphosphate Directly Regulates Btk," *J. Biol. Chem.* 276(19), 16201-16206.
60. Saito, K. et al. (2003) "Btk Regulates Ptdins-4,5-P2 Synthesis: Importance for Calcium Signaling and Pi3k Activity," *Immunity* 19(5), 669-678.
61. Li, Z. et al. (1997) "Phosphatidylinositol 3-Kinase-Gamma Activates Bruton's Tyrosine Kinase in Concert with Src Family Kinases," *Proc. Natl. Acad. Sci. U. S. A* 94(25), 13820-13825.
62. Bruyere, C. et al. (2011) "Temozolomide Modifies Caveolin-1 Expression in Experimental Malignant Gliomas in vitro and in vivo," *Transl. Oncol.* 4(2), 92-100.
63. Sagiv-Barfi, I. et al. (2015) "Therapeutic Antitumor Immunity by Checkpoint Blockade Is Enhanced by Ibrutinib, an Inhibitor of Both Btk and Itk," *Proc. Natl. Acad. Sci. U. S. A* 112(9), E966-972.

64. Wang, X. et al. (2013) "Ppargamma Maintains Erbb2-Positive Breast Cancer Stem Cells," *Oncogene* 32(49), 5512-5521.
65. Wang, X. and Zhao, J. (2007) "Klf8 Transcription Factor Participates in Oncogenic Transformation," *Oncogene* 26(3), 456-461.

We claim:

1. A method of treating breast cancer, comprising:
   a) providing
      i) a subject comprising a Bruton's tyrosine kinase-C positive breast cancer, said cancer having an AKT or EGF signaling pathway;
      ii) a composition comprising a Bruton's tyrosine kinase inhibitor and an EGFR inhibitor, and
   b) treating said subject with said composition, wherein said Bruton's tyrosine kinase inhibitor blocks said AKT or EGF signaling pathway:
   c) preventing resistance development of said breast cancer to said EGFR inhibitor due to said blocked AKT or EGF signaling pathway.

2. The method of claim 1, wherein said breast cancer is further a $HER2^+$ breast cancer.

3. The method of claim 1, wherein said Bruton's tyrosine kinase is a variant comprising an amino-terminal extension.

4. The method of claim 1, wherein said EGFR inhibitor is lapatinib.

5. The method of claim 1, wherein said EGFR inhibitor is selected from the group consisting of gefitinib, erlotinib, cetuximab, panitumumab, and vandetanib.

6. The method of claim 1, wherein said Bruton's tyrosine kinase inhibitor is selected from the group consisting of ibrutinib (PCI-32765), AVL-292 and CGI-1746.

7. The method of claim 1, wherein treating with said composition results in reduced proliferation of at least some of said cancer cells within said subject.

* * * * *